US007881878B2

(12) United States Patent
Burrus et al.

(10) Patent No.: US 7,881,878 B2
(45) Date of Patent: Feb. 1, 2011

(54) SYSTEMS, DEVICES, AND METHODS FOR DIFFUSION TRACTOGRAPHY

(75) Inventors: Nicolas Burrus, Lardy (FR); Mariappan S. Nadar, Plainsboro, NJ (US)

(73) Assignee: Siemens Medical Solutions USA Inc., Malvern, PA (US)

( * ) Notice: Subject to any disclaimer, the term of this patent is extended or adjusted under 35 U.S.C. 154(b) by 1035 days.

(21) Appl. No.: 11/398,189

(22) Filed: Apr. 5, 2006

(65) Prior Publication Data

US 2006/0229856 A1 Oct. 12, 2006

Related U.S. Application Data

(60) Provisional application No. 60/670,211, filed on Apr. 11, 2005.

(51) Int. Cl.
*G01N 31/00* (2006.01)
(52) U.S. Cl. .......................................... 702/28; 600/410
(58) Field of Classification Search ........................ None
See application file for complete search history.

(56) References Cited

U.S. PATENT DOCUMENTS

| 5,969,524 | A  |    | 10/1999 | Pierpaoli |         |
|-----------|----|----|---------|-----------|---------|
| 6,642,716 | B1 | *  | 11/2003 | Hoogenraad et al. | 324/309 |
| 6,992,484 | B2 |    | 1/2006  | Frank     |         |

OTHER PUBLICATIONS

Parker et al. (IPMI 2003, LNCS 2732, pp. 684-695, 2003).*
Alexander et al., Magnetic Resonance in Medicine 45:770-780 (2001).*
Weisstein, Eric W. "Transpose." From MathWorld—A Wolfram Web Resource. [online] mathworld.wolfram.com/Transpose.html; accessed on Oct. 22, 2009.*
Arulampalam, S., et al., "A Tutorial on Particle Filters for On-Line Non-Linear/Non-Gaussian Bayesian Tracking", IEEE Transactions on Signal Processing, Jan. 1, 2002, 174-188 page(s), vol. 50/2, IEEE.
Basser, P., "In Vivo Fiber Tractography Using DT-MRI Data", Magnetic Resonance in Medicine, Jun. 5, 2000, 625-632 page(s), vol. 44, Wiley-Liss, Inc., US.
Bjornemo, M., "Regularized Stochastic White Matter Tractography Using Tensor MRI", MICCAI 2002, Jan. 1, 2002, 8 page(s).
Brun, A., et al., "White Matter Tractography Using Sequential Importance Sampling", Proceedings of the ISMRM Annual Meeting (ISMRM'02), Jan. 1, 2002, 1 page(s), vol. 10.
Cabral, B., "Imaging Vector Fields Using Line Integral Convolution", Computer Graphics Proc., Jan. 1, 1993, 263-270 page(s).
Hagmann, P., "DTI Mapping of Human Brain Connectivity: Statistical Fibre Tracking and Virtual Dissection", NeuroImage, Jan. 1, 2003, 545-554 page(s), vol. 19, Elsevier Science.
Interrante, V., "Strategies for Effectively Visualizing 3D Flow with vol. LIC", Proceedings of Visualization '97, Jan. 1, 1997, 421-424 page(s).
Laramee, R., "The State of the Art in Flow Visualization: Dense and Texture-Based Techniques", Computer Graphics Forum, Jan. 1, 2004, 203-221 page(s), vol. 22/2.
Lazar, M., "White Matter Tractography Using Diffusion Tensor Deflection", Human Brain Mappling, Jan. 1, 2003, 306-321 page(s), vol. 18, Wiley-Liss, Inc.
McGraw, T., "DT-MRI Denoising and Neuronal Fiber Tracking", Medical Image Analysis, Jan. 1, 2004, 95-111 page(s), vol. 8, Elsevier, US.
McGraw, T., "Neuronal Fiber Tracking in DT-MRI", Master's Thesis, Jan. 1, 2002, University of Florida, US.
Parker, G., "Estimating Distributed Anatomical Connectivity Using Fast Marching Methods and Diffusion Tensor Imaging", IEEE Transactions on Medical Imaging, May 1, 2002, 505-512 page(s), vol. 21/5, IEEE.
Pennec, X., "A Riemannian Framework for Tensor Computing", Rapport de Recherche, INRIA, Jul. 1, 2004, 36 page(s), France.
Post, F., "The State of the Art in Flow Visualization: Feature Extraction and Tracking", Computer Graphics Forum, Jan. 1, 2003, 1-17 page(s), vol. 22/4, Blackwell Publishers.
Poupon, C., "Towards Inference of the Human Brain Connectivity from MR Diffusion Tensor Data", Medical Image Analysis, Jan. 1, 2001, 1-15 page(s), vol. 5, Elsevier.
Rezk-Salama, C., "Interactive Exploration of Volume Line Integral Convolution Based on 3D-Texture Mapping", IEEE Visualization '99, Jan. 1, 1999, 233-240 page(s), IEEE, Germany.
Shen, H., "Visualizing Vector Fields Using Line Integral Convolution and Dye Advection", Symposium on Volume Visualization, Jan. 1, 1996, 63-70 page(s).
Stalling, D., "Fast and Resolution-Independent Line Integral Convolution", Computer Graphics Proceedings, Annual Conference Series, Jan. 1, 1995, 249-256 page(s).
Tschumperie, D., "PDE's Based Regularization of Multivalued Images and Applications", PhD Thesis, Jan. 1, 2002, Universite de Nice-Sophia Antipolis.
Tschumperie, D., "Tensor Field Visualization with PDE's and Application to DT-MRI Fiber Visualization", Procedure of Variational and Level Set Methods, Jan. 1, 2003.
Westin, C., "Processing and Visualization for Diffusion Tensor MRI", Medical Image Analysis, Jan. 1, 2002, 93-108 page(s), vol. 6, Elsevier.
Zhang, S., "Visualizing Diffusion Tensor MR Images Using Streamtubes and Streamsurfaces", IEEE Transactions on Visualization and Computer Graphics, Oct. 1, 2003, 454-462 page(s), vol. 9/4, IEEE.
Zhukov, L., "Oriented Tensor Reconstruction: Tracing Neural Pathways from Diffusion Tensor MRI", IEEE Visualization 2002, Oct. 27, 2002, 8 page(s), IEEE.
Coulon, Olivier et al., "A Regularization Scheme for Diffusion Tensor Magnetic Resonance Images," M.F. Insana, R.M. Leahy (Eds.): IPMI2001, LNCS 2082 pp. 92-105, 2001.
Kindlmann, Gordon et al., "Strategies for Direct Volume Rendering of diffusion Tensor Fields," Scientific Computing and Imaging Department of Computer Science, University of Utah Visualization and Computer Graphics, IEEE Transactions on Apr.-Jun. 2000 6(2): 124-138.

* cited by examiner

*Primary Examiner*—Karlheinz R Skowronek

(57) ABSTRACT

Certain exemplary embodiments comprise a method, which can comprise automatically causing a representation of body tissue to be rendered. The body tissue can be tracked via clusters. The clusters each can comprise a predetermined number of particles. Each particle of a particular cluster can be representative of a discreet path associated with the particular cluster in a tensor field.

17 Claims, 29 Drawing Sheets

(a)            (b)

29000

SYSTEMS, DEVICES, AND METHODS FOR DIFFUSION TRACTOGRAPHY

CROSS-REFERENCES TO RELATED APPLICATIONS

This application claims priority to, and incorporates by reference herein in its entirety, pending U.S. Provisional Patent Application Ser. No. 60/670,211, filed 11 Apr. 2005.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Figure 1:
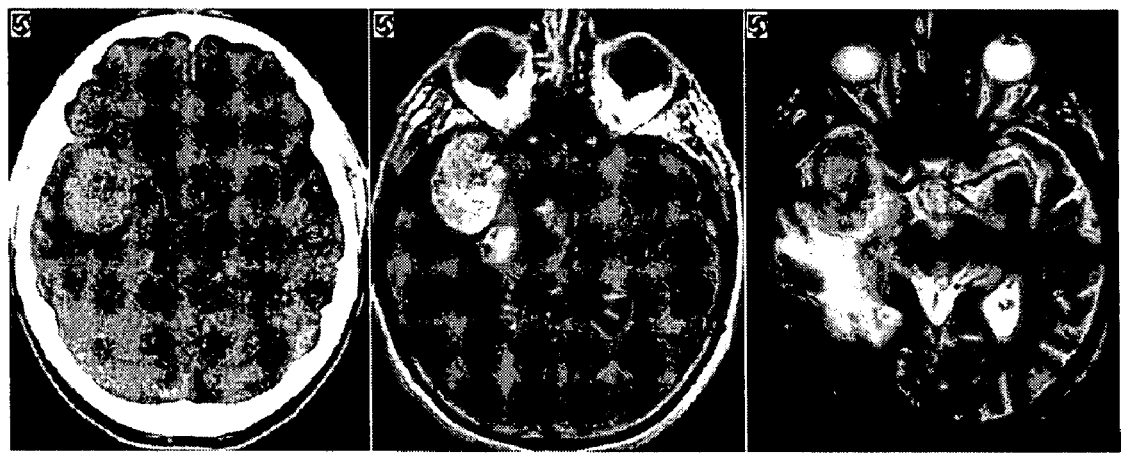
FIG. 1 illustrates exemplary renderings of a human brain.

Certain exemplary embodiments comprise a method, which can comprise automatically causing a representation of body tissue to be rendered. The body tissue can be tracked via clusters. The clusters each can comprise a predetermined number of particles. Each particle of a particular cluster can be representative of a discreet path associated with the particular cluster in a tensor field.

Certain exemplary embodiments comprise brain imaging, such as an in-vivo brain analysis tool. To get a better understanding of brain internals, certain exemplary embodiments can combine several kind of information, such as:
anatomic images using high resolution Computed Tomography (CT);
functional activation using Functional Magnetic Resonance Imaging (F-MRI); and/or
connectivity using Diffusion Tensor Magnetic Resonance Imaging (DT-MRI); etc.

Diffusion tensor images can provide information about water diffusion. The acquisition process can result in a volume of tensors where each voxel describes the local spatial behavior of water molecules. Diffusion properties can be good clues about underlying geometric structures, such as:
fibers connecting different regions of the brain, which can induce anisotropic water diffusion, like in a tube; and/or
gray matter, without particular structure, which can induce isotropic diffusion; etc.

Thus, by using DT-MRI data, certain exemplary embodiments can infer some information about fibers and connectivity. Certain exemplary embodiments can find accurate and efficient techniques to visualize diffusion tensor volumes.

Exemplary Embodiments Can Comprise:
global visualization of a diffusion volume; and/or
individual fiber bundles localization, using tracking algorithms; etc.

Global visualization techniques can provide an overview of brain geometry. By reducing the diffusion information in each voxel to a main diffusion direction, vector field's visualization algorithms can be applied. Certain exemplary embodiments can utilize LIC (Line Integral Convolution) on 2D slices of the brain. Certain exemplary embodiments can improve an LIC algorithm to make the LIC algorithm usable in real applications. The algorithm was applied to three-dimensional (3D) portions of a vector field, but the results were rather dense and hard to interpret. To bring more flexibility, a Partial Differential Equation (PDE) based technique, able to handle the whole diffusion data, was adapted and implemented. The approach appeared to be flexible enough to find some applications in 3D, but a complete representation of the diffusion volume was still complicated to interpret. In addition to global visualization, fiber bundles localization, avoiding density problems, was considered.

Diffusion tensor data can be rather noisy and limited in resolution, raising partial volume effects errors. Moreover, fibers can split into several branches and cross other fibers, leading to ambiguities. For performance reasons, only local approaches to tracking have been taken into account. Certain exemplary embodiments can comprise Kalman filters to handle the noise of DT-MRI data during the tracking process. However, Kalman filters might be restricted to Gaussian noise and linear evolution functions. Particle filters can be used in numerous difficult tracking problems, involving noise or multi-modality (several possible targets). Particle filters might not be directly applicable to fiber tracking though, but the general technique behind them, SISR (Sequential Importance Sampling Resampling) can still be used. This approach can provide a flexible framework to design probabilistic walks. An arbitrarily complex probability can be defined to drive a tracking process, taking into account many parameters in addition to diffusion directions, such as regularity or a degree of anisotropy.

In certain exemplary embodiments, SISR can be applied to fiber tracking. The resulting algorithm can handle both noise and ambiguities raised by partial volume effects and crossing fibers. Combined with a simple clustering algorithm, distinct fiber branches can be explored without a loss of tracking power. Interesting results were obtained with a reasonable computation time. The flexibility of the framework can make it possible to add many parameters to the model.

Certain exemplary embodiments can comprise an in-vivo brain analysis tool. To get a better understanding of the brain internals, several kind of information can be combined:
anatomic images using high resolution CT;
functional activation using F-MRI; and/or
connectivity using DT-MRI; etc.

Emphasis can be placed on the third item. Diffusion tensor images can provide information about water diffusion. An acquisition process results in a volume of tensors where each voxel can describe a local spatial behavior of water molecules. Diffusion properties can be clues about underlying geometric structures, such as:
fibers connecting different regions of the brain induce highly anisotropic water diffusion, like in a tube; and/or
gray matter, without particular structure, induces isotropic diffusion; etc.

Thus, by using DT-MRI data, it might be possible to infer some information about fibers and connectivity. Certain exemplary embodiments can find accurate and efficient techniques to visualize diffusion tensor volumes. Possible approaches can comprise:
global visualization of the whole diffusion tensor volume; and/or
individual fiber localization, using tracking algorithms; etc.

A goal of DT-MRI can be to analyze water diffusion properties. Diffusion can be represented by second order tensors, which have nice mathematical properties, making them handy to use. Second orders tensors and DT-MRI in can have limitations, such as noise, partial volume effects or branching.

FIG. 1 illustrates exemplary renderings of a human brain. Animal and human brains can be complex structures. Connectivity can be effected by myelin fibers, which can define small geometrical patterns. Unfortunately, myelin fibers might not appear on traditional medical images issued by techniques such as Computerized Tomography (CT) or Magnetic Resonance (MR), as shown on FIG. 1, which illustrates an exemplary CT image on the (left), an exemplary T1 weighted MR image in the center, and an exemplary T2 weighted MR image on the right. White matter of the brain, composed of complex geometrical structures, appears as homogeneous.

DT-MRI can be configured to render such complex structures in human and rat brains. DT-MRI can be an in-vivo imaging technique that determines information related to rendering complex structures.

Figure 2:
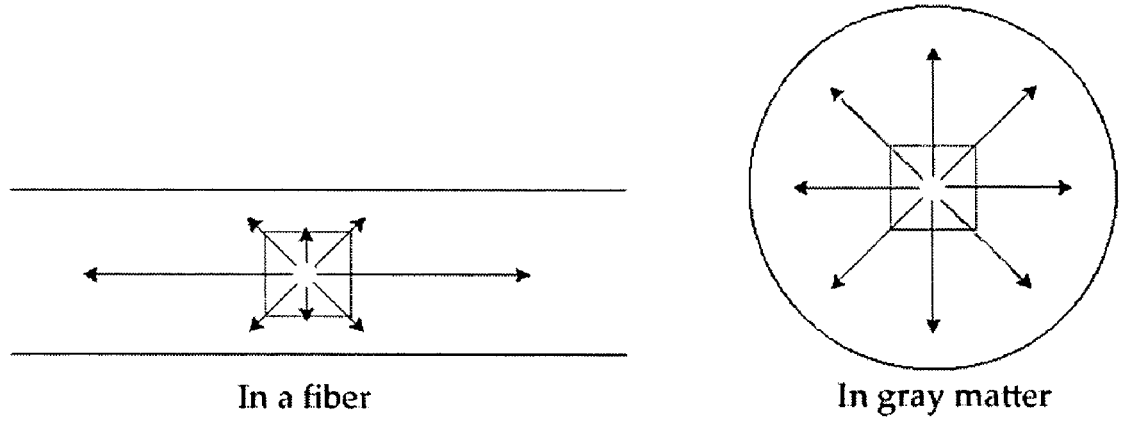
FIG. 2 is a diagram of exemplary diffusion vectors.

FIG. 2 is a block diagram of exemplary diffusion vectors. Water molecules can have a random motion, called Brownian motion. In homogeneous regions, a global displacement of the molecules can be approximately identically constrained in every direction, which can lead to an isotropic diffusion. This means water molecules might go into any direction with approximately the same probability. However, in presence of fibers, as in muscular tissues or brain white matter, molecules displacements can be constrained along fiber borders, as in blotting paper. This is illustrated in FIG. 2. In a fiber, diffusion of water can be substantially anisotropic, whereas in homogeneous areas, such as gray matter, diffusion can be substantially isotropic.

DT-MRI can be based on diffusion Magnetic Resonance Imaging (MRI), which can be based on MRI. Using nuclear spinning properties of hydrogen atoms, MRI scanners can send a radio frequency pulse to the desired area, and non-intrusively gather several information, such as:
quantity of water molecules;
chemical surrounding of the water (T1 relaxation); and/or
chemical surrounding of each individual hydrogen atoms (T2 relaxation), which gives a different contrast than T1; etc.

By applying two symmetric additional magnetic gradients in a particular direction, Diffusion MRI can analyze the diffusion coefficient of water molecules in a gradient's direction. This diffusion coefficient can be related to a quantity of water, which moved into the gradient's direction during the acquisition time.

Diffusion can be a three-dimensional process; so to capture diffusion properties six diffusion MRI three-dimensional images in six different directions can be acquired. An additional scan can be performed without any gradient field to normalize results. The six directions can be chosen to be non-coplanar to get a good representation of a three-dimensional diffusion, such as $(1, 0, 0)$; $(0, 1, 0)$; $(0, 0, 1)$; $(1, 1, 0)$; $(1, 0, 1)$; $(0, 1, 1)$. Six axes can be sufficient since the diffusion can be symmetric. From seven diffusion-weight images, one three-dimensional tensor field can be built, such as by solving a system of Stejskal-Tanner equations. Certain exemplary embodiments can comprise any of several system resolution methods. Each tensor can aggregate six diffusion coefficients into a mathematical tool.

In a three-dimensional space, a second order tensor D can be represented by a 3×3 matrix, positive, symmetric and real:

$$D = \begin{pmatrix} D_{xx} & D_{xy} & D_{xz} \\ D_{yx} & D_{yy} & D_{yz} \\ D_{zx} & D_{zy} & D_{zz} \end{pmatrix} \quad (2.1)$$

where $D_{xx}$ can correspond to diffusion along an x direction, $D_{xy}$ to diffusion along an xy direction, and so forth. This matrix can be symmetric such that $D_{ij}=D_{ji}$.

A norm of a tensor D can be defined by:

$$\|D\|^2 = \sum_{ij} D_{ij}^2 = \sum_{k} \lambda_k^2$$

where the $\lambda_k$ are the eigenvalues of D. In certain exemplary embodiments, diffusion tensors can be normalized in a preprocessing step.

The diffusion coefficient in an arbitrary direction $\vec{d}$ can be calculated with a tensorial dot product:

diffusion$(D,d)=d^T.D.d$

This can be useful to determine how a particular diffusion direction is compatible with an observed tensor. In particular, any direction can be compatible with an isotropic tensor (D=Id).

Information encapsulated in a tensor can be understood via considering eigenvalues and eigenvectors of an associated matrix. The eigenvectors can represent main diffusion axes, and corresponding eigenvalues can represent the diffusion coefficient for each axis. A tensor can be defined by an eigensystem:

$$D = \sum_{k} \lambda_k \times e_k^T e_k$$

where $\lambda_k$ is the k-nth eigenvalue and $e_k$ the k-nth eigenvector. In the following, the eigenvalues will be considered to be ordered following their indice: $\lambda_1 \geq \lambda_2 \geq \lambda_3$.

Figure 3:
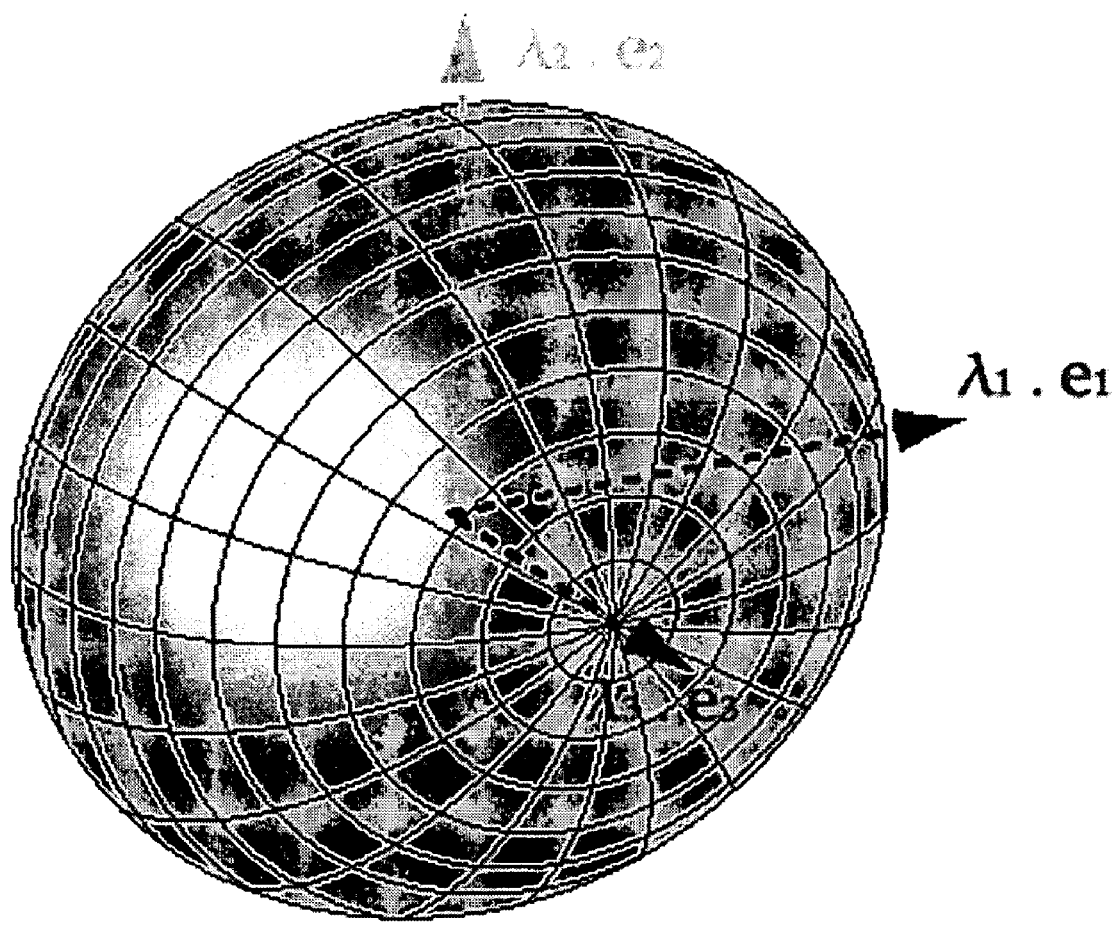
FIG. 3 is a diagram of exemplary eigenvectors.

FIG. 3 is a diagram of exemplary eigenvectors. Due to properties of D, the eigenvalues can be real and positive and the eigenvectors can be orthogonal to each other. The eigensystem can provide an intuitive way to interpret a diffusion tensor. FIG. 3 shows how tensors can be graphically represented using a three-dimensional ellipsoid. In FIG. 3 eigenvectors define a basis, and weighting of an axis length by the eigenvalues. In certain exemplary embodiments, an overview of tensor can be obtained via utilizing a three-dimensional ellipsoid.

Eigenvalues can be a criterion to determine an anisotropic level of diffusion:

if $\lambda_1 = \lambda_2 = \lambda_3$, the region can be considered to be substantially isotropic, and there might be no predominant diffusion direction;

if $\lambda_1 = \lambda_2 \gg \lambda_3$, the area can be partially anisotropic, but can still be isotropic in a plane defined by $e_1$ and $e_2$;

if $\lambda_1 \gg \lambda_2 = \lambda_3$, the diffusion can be substantially anisotropic, such as in a main particular direction. FIG. 3 illustrates the categories of shapes with ellipsoids.

Figure 4:
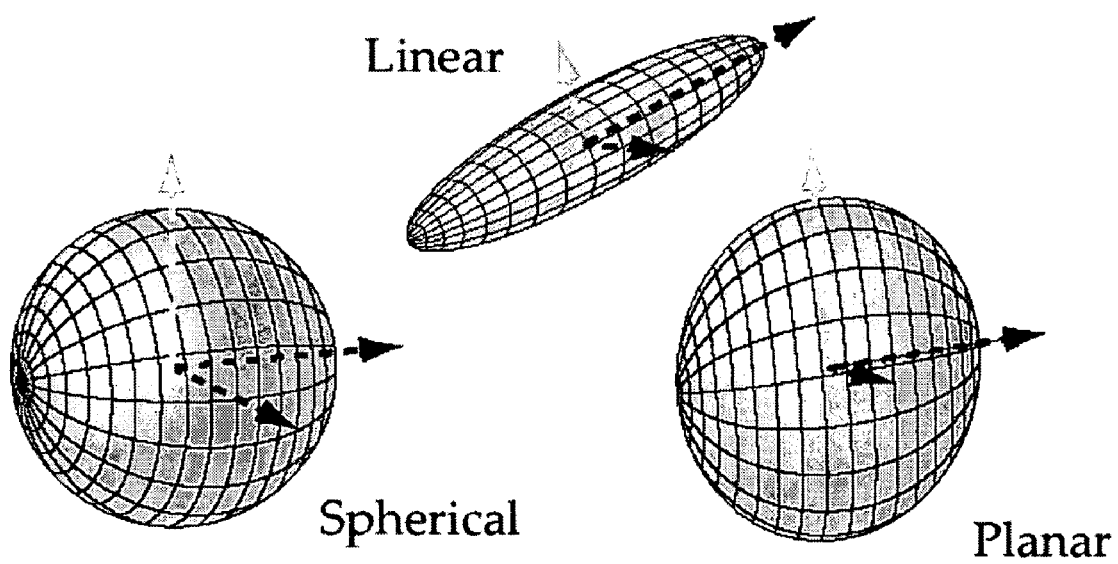
FIG. 4 is a diagram of exemplary ellipsoids.

FIG. 4 is a diagram of exemplary ellipsoids. A linear ellipsoid (cigar-shaped) can represent a substantially anisotropic diffusion, a planar one (pancake-shaped) can correspond to substantially two-dimensional (2d) isotropic diffusion, and a spherical ellipsoid can result from substantially isotropic diffusion.

Figure 5:
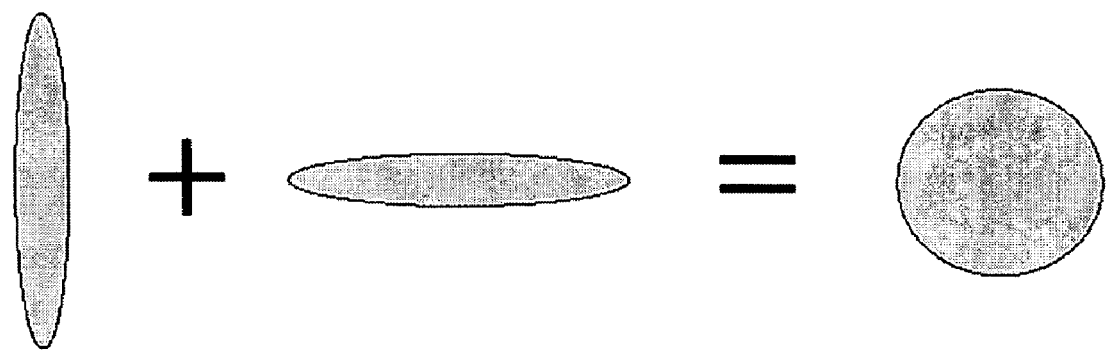
FIG. 5 is a diagram of exemplary tensors.

FIG. 5 is a diagram of exemplary tensors. A sum of two tensors can be equivalent to a sum of two matrices. The sum can have some inconvenient geometric properties, the shape of the input tensors is not invariant by addition, as illustrated in FIG. 5. The sum of two highly anisotropic tensors can result in a substantially isotropic tensor.

An acquisition resolution can be substantially anisotropic, a number of slices can be less important than a number of rows and columns. In addition, some tracking algorithms might need continuous displacements within the tensor volume, so tensor interpolation can be used to obtain tensor values between acquired voxels.

Tensor interpolation methods can comprise:

Nearest neighbor;

Trilinear interpolation; and/or

Raw data interpolation; etc.

The nearest neighbor method can provide relatively coarse results and might not be suitable for continuous process such as fiber tracking. However, in texture-based global visualization techniques nearest neighbor interpolation can provide acceptable results. The nearest neighbor method can be relatively secure in that meaningless, badly shaped tensors with a biased interpolation might not be created.

The trilinear interpolation method can be used for interpolation in 3D spaces. Linear interpolation can be chosen for relative simplicity and efficiency. Linear interpolation can be applied to tensors easily, by linearly interpolation the matrix coefficient. Linear interpolation can provide valid tensors. A drawback of linear interpolation can be a loss of boundaries: interpolating two substantially anisotropic tensors may result in a substantially isotropic tensor.

In raw data interpolation, tensors can be computed from several raw diffusion-weighted images data, acquired from a scanner along different gradient directions. Each image can be scalar valued, so instead of directly interpolating tensors, raw diffusion coefficients can be directly interpolated, and a new tensor computed. This approach can be theoretically stronger, but implies additional Stejskal-Tanner system solving, which can be slower than linear interpolation.

Certain exemplary embodiments can utilize other methods, generally trying to preserve boundaries, such as cubic interpolation, anisotropic interpolation, and/or a Riemann framework, etc. In certain exemplary embodiments, trilinear interpolation can be utilized, for its simplicity and efficiency.

Though DT-MRI data can provide a lot of information, DT-MRI data might be difficult to handle with straightforward methods. Several uncertainty parameters can make a design of robust DT-MRI algorithms difficult.

Figure 6:
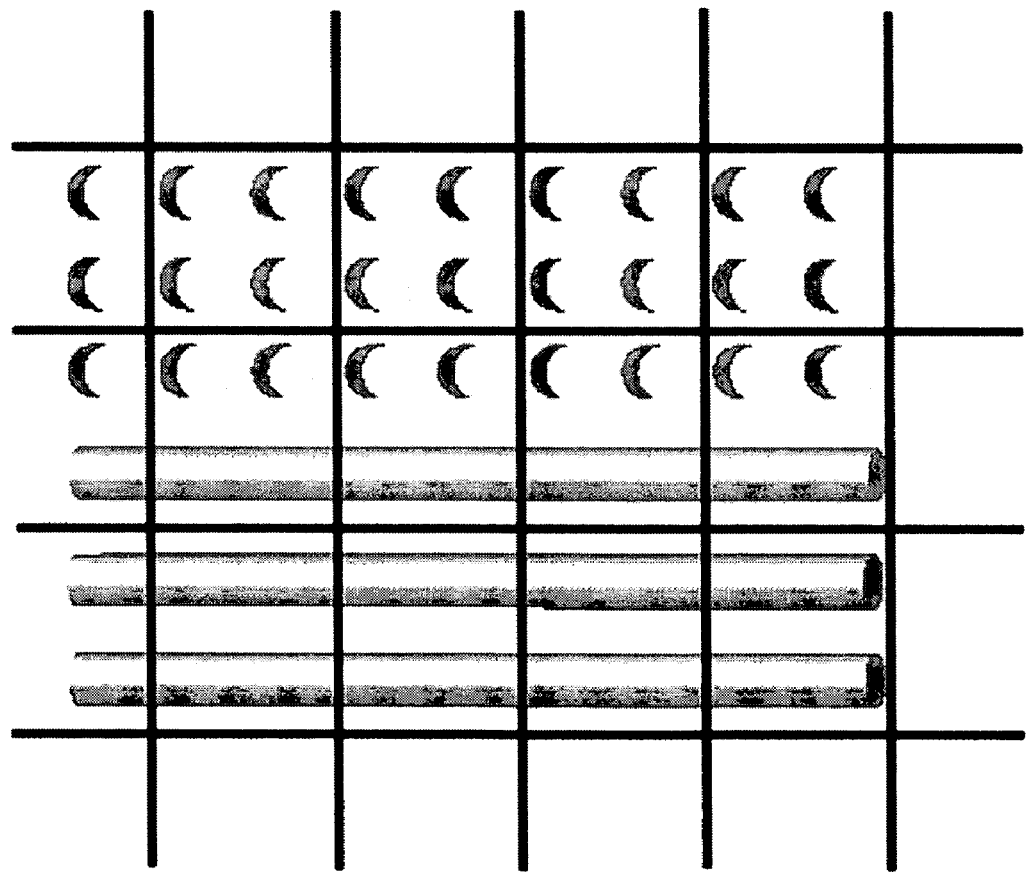
FIG. 6 is a diagram of exemplary diffusion tensors.

FIG. 6 is a diagram of exemplary diffusion tensors. Magnetic Resonance scanners can have a rather low resolution; the size of DTMRI voxels can be $1.7 \times 1.7 \times 3$ mm$^3$. Brain fibers can be much thinner, in the order of a micron. This can lead to partial volume effects: fibers with different directions may be regrouped within a given tensor. This is depicted in FIG. 6. The resulting tensor can be a sum of partial tensors corresponding to combined directions. A combination of two substantially anisotropic tensors can give a substantially isotropic tensor, this means that even in substantially anisotropic regions comprising fibers, substantially isotropic tensors may appear. Increasing scanner resolution can help to a certain extent, but the size order of fibers can be too small to avoid partial volume effects. In the middle row of FIG. 6, the diffusion tensors can be the average of two different directions.

DT-MRI data can be noisy. Noise can be accumulated during image acquisition and the subject himself might add thermal noise. It can be shown that MR noise follows a Rician distribution. Any of several methods can be utilized to remove this Rician noise. However, in most cases, MR noise can be modeled by a Gaussian noise, which can be a good approximation for certain signal to noise ratios.

Figure 7:
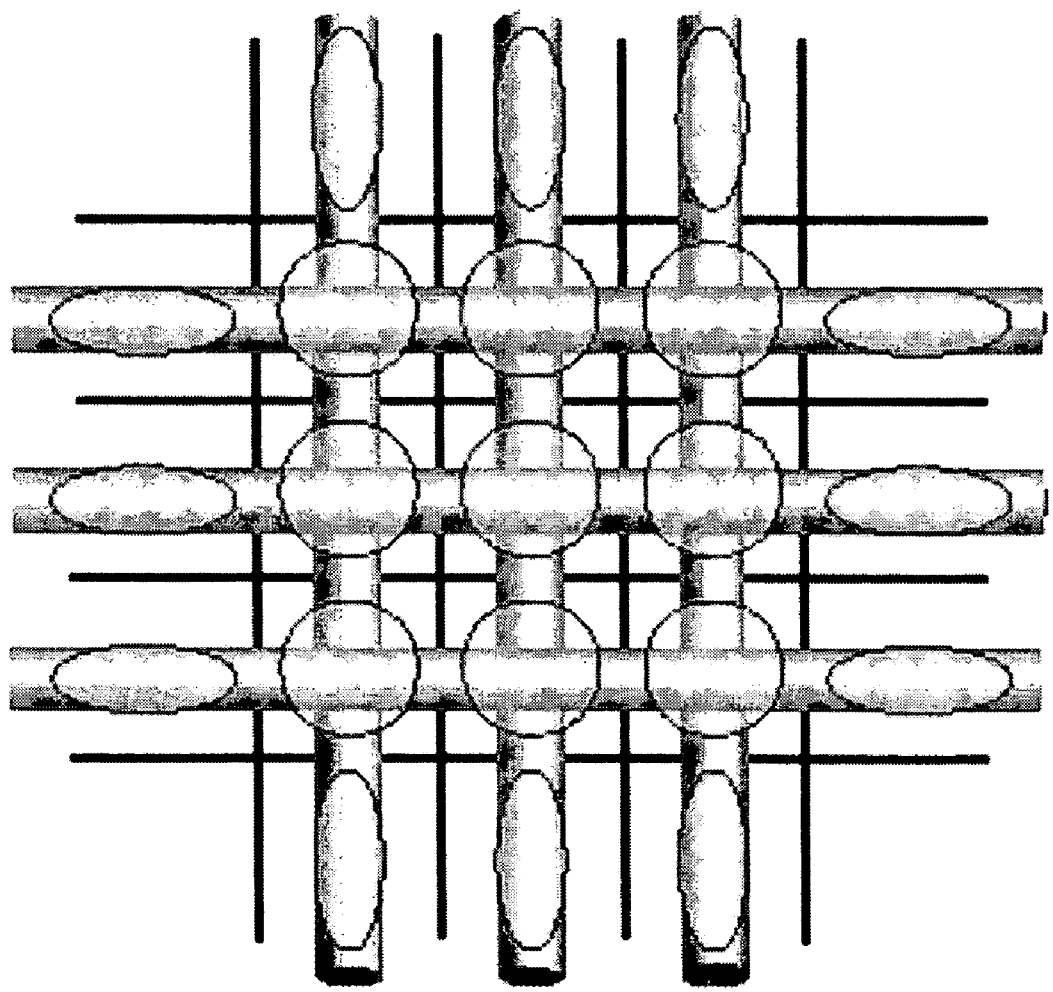
FIG. 7 is a diagram of exemplary fibers.

FIG. 7 is a diagram of exemplary fibers. Two considerations can increase a difficulty of fiber path determination: crossing fibers and branching fibers. Some fibers might cross other fibers. A tensor might only encode one diffusion direction. So resulting tensors in crossing points can be a combination of two underlying fibers directions. This can be problematic. FIG. 7 shows a tensor field corresponding to crossing fibers. Robust algorithms might be utilized to cope with ambiguities in crossing points. FIG. 7 shows crossing fibers, which can generate isotropic tensors and lead to ambiguities.

Figure 8:
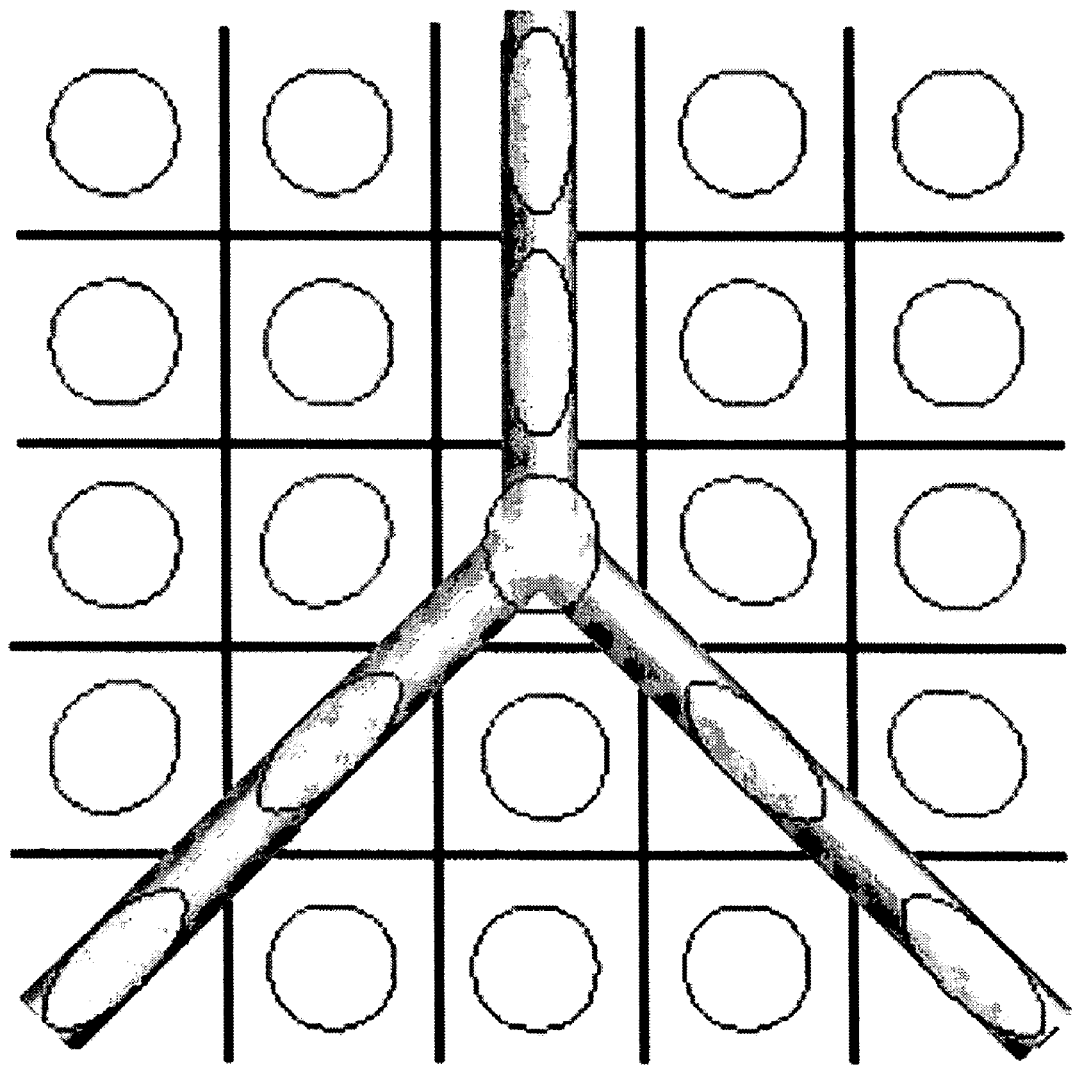
FIG. 8 is a diagram of an exemplary branching fiber.

FIG. 8 is a diagram of an exemplary branching fiber. One fiber might divide into several sub-fibers. Branching can create ambiguities at the branching points, as illustrated in FIG. 8. In FIG. 8 a branching fiber can provide a substantially isotropic tensor at the branching point.

Evaluating a fiber tracking method can be an issue. No method is known to have received a clinical validation, and no fully segmented dataset is known to be available for comparison purposes. Thus, validation might only be done on generated datasets, or by the appreciation of an expert knowledgeable regarding anatomical plausibility of detected structures.

In certain exemplary embodiments, no assumption about the underlying structures need be made, certain exemplary techniques can be applied to any DT-MRI dataset. A potential approach to represent tensor fields can comprise reducing each tensor to a scalar value, and then utilizing scalar-valued volume visualization. In DT-MRI, information can comprise a degree of anisotropy. In certain exemplary methods, a degree of anisotropy can depend on a chosen gradient direction. Fractional Anisotropy Factional Anisotropy (FA), can be defined by:

$$FA = \sqrt{\frac{3}{2}} * \sqrt{\frac{(\lambda_1 - \bar{\lambda})^2 + (\lambda_2 - \bar{\lambda})^2 + (\lambda_3 - \bar{\lambda})^2}{\lambda_1^2 + \lambda_2^2 + \lambda_3^2}}$$

where $\lambda_1, \lambda_2, \lambda_3$ are eigenvalues and $\bar{\lambda}$ is the mean eigenvalue:

$$\bar{\lambda} = \frac{\lambda_1 + \lambda_2 + \lambda_3}{3}.$$

FA can measure how inhomogeneous diffusion coefficients might be along main directions. Thus, FA=0 can mean all the diffusion coefficients are approximately equal and the tensor might be substantially isotropic. A value of FA=1 can mean the tensor might be substantially linear-shaped, and there might be a primary diffusion direction. Shape measures FA measures how anisotropic the tensor might be, but does not necessarily provide an indication of a tensor shape. Cigar-shaped and pancake-shaped tensors might have similar FA values. To discriminate shape information, several scalar measures can be utilized, such as:

linear diffusion:

$$c_l = \frac{\lambda_1 - \lambda_2}{\lambda_1},$$

how close measured diffusion is to a perfect line;

planar diffusion:

$$c_p = \frac{\lambda_2 - \lambda_3}{\lambda_1},$$

how close measured diffusion is to a perfect plane; and
and spherical diffusion:

$$c_s = \frac{\lambda_3}{\lambda_1};$$

etc.

By construction $c_l + c_p + c_s = 1$.

Figure 9:
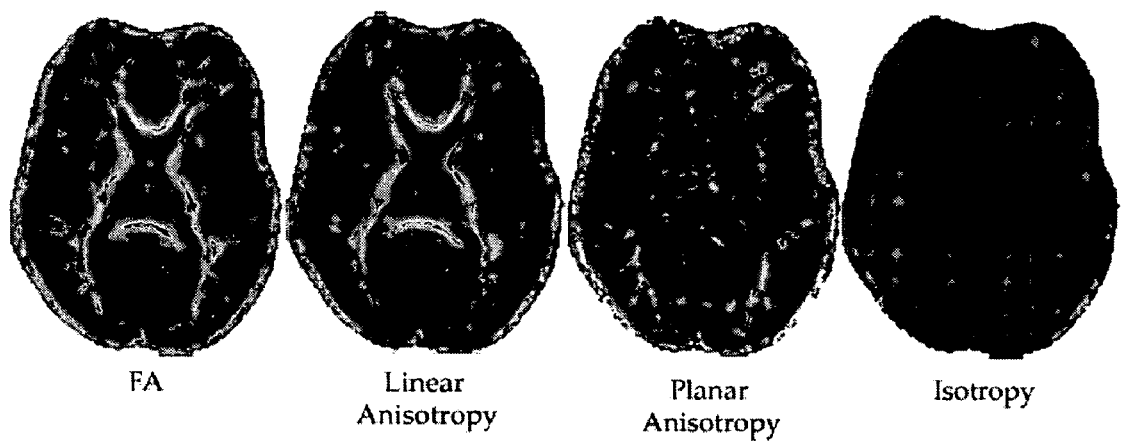
FIG. 9 is a diagram of exemplary axial slices of an exemplary brain.

FIG. 9 is a diagram of exemplary axial slices of an exemplary brain. FIG. 9 gives an overview of the different scalar measures. FIG. 9 provides a comparison of scalar measures on an axial slice of the brain.

Figure 10:
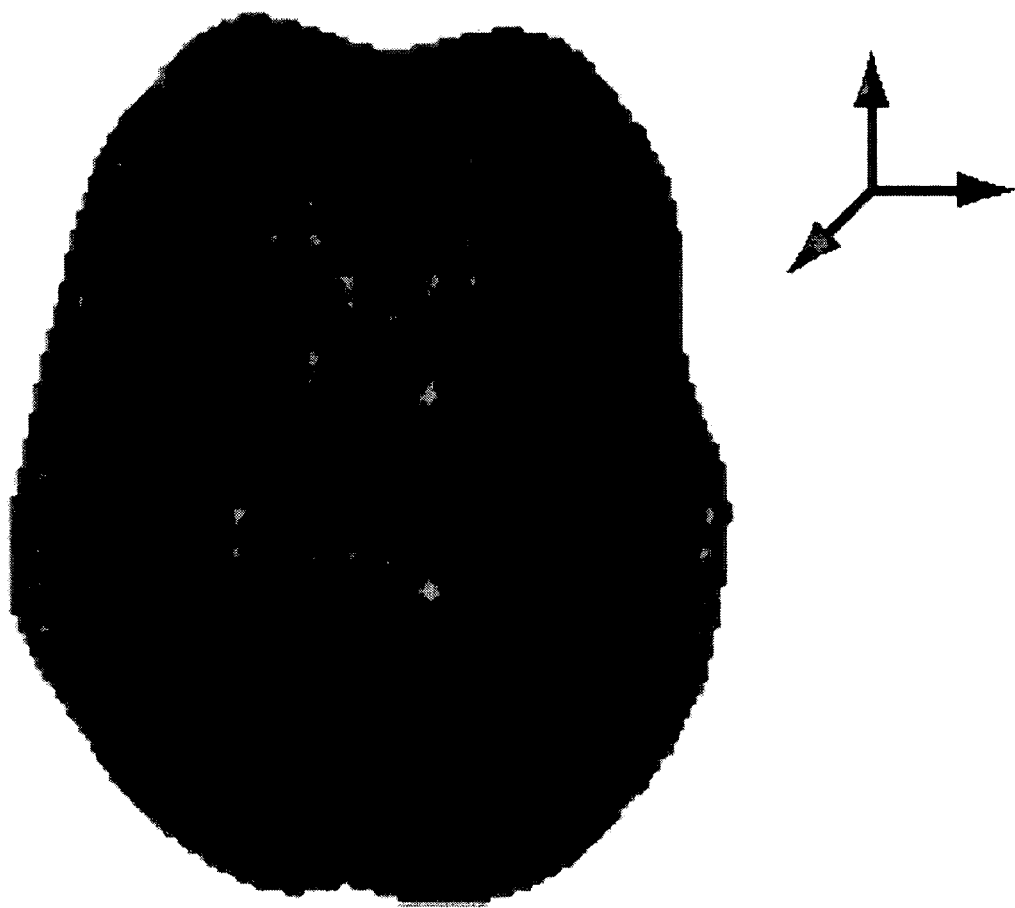
FIG. 10 is a diagram of an exemplary eigenvector map on an axial slice of an exemplary brain.

By extracting the main eigenvector of a tensor, a three-dimensional principal direction can be encoded, by a color, simply by mapping each x, y, z component to an r, g, b component. This technique can be used with other visualization algorithms, as a postprocessing step, FIG. 10 is a diagram of an exemplary eigenvector color map on an axial slice of an exemplary brain. FA can determine color intensity for a color map. FIG. 10 shows results of postprocessing a FA image with an eigenvector color map. Some color spaces can be more convenient to act on the luminosity. For example, in certain applications, HSV can be used instead of RGB, through a simple transformation.

Scalar values can be relevant to identify regions where structures can be found, but might not provide information about the actual diffusion directions. Tensor can be mapped to an ellipsoid. Glyphs-based methods can be based on this idea, they represent at each voxel the glyph corresponding to the diffusion tensor. Several kind of glyphs can be used, which can comprise ellipsoids, boxes and/or superquadrics, etc. An advantage of glyph based methods can be accuracy. A glyph can describe a corresponding tensor. However, glyphs can be sensitive to noise and limit resolution, each glyph taking a lot of place.

Figure 11:
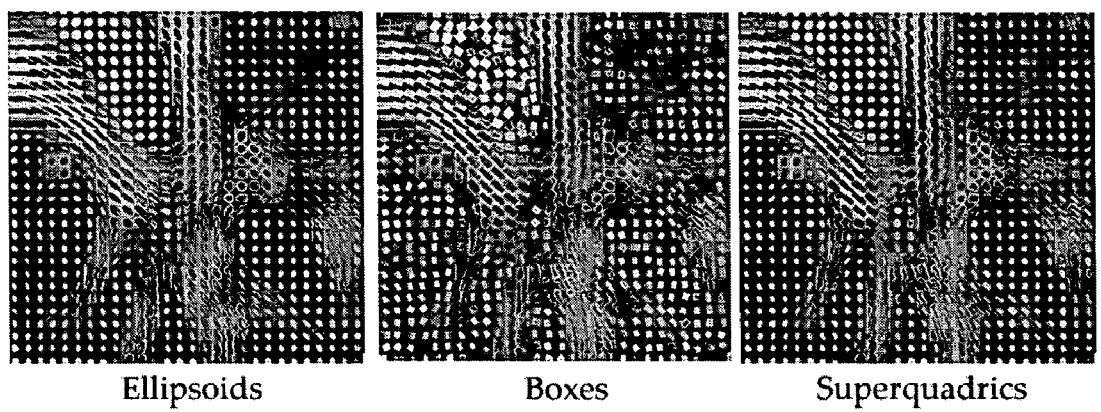
FIG. 11 is a diagram of exemplary glyphs-based representations of synthetic data.

FIG. 11 is a diagram of exemplary glyphs-based representations of synthetic data. Results with different kind of glyphs are given in FIG. 11.

Instead of considering a whole tensor, certain exemplary embodiments can reduce the tensor to one vector, comprising a principal diffusion direction (PDD). By reducing each tensor to a main eigenvector, tensor field visualization can be simplified into a vector field or flow visualization problem. Line Integral Convolution (LIC) can be a flow visualization algorithm. Texture-based, LIC can accurately render high curvature details and generate high resolution images. In addition, LIC can be robust to noisy data.

For the sake of simplicity, LIC can be described in two dimensions only. LIC can be a dense, texture-based method. The input to an LIC algorithm can be a randomly noised texture and a vector field. The output can be an initial random texture, with noise correlated to follow a flow given by an input vector field.

Figure 12:
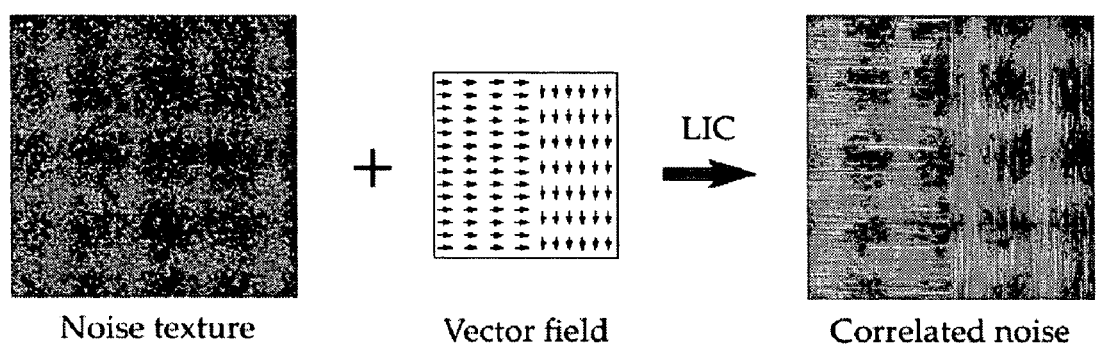
FIG. 12 is a diagram of an exemplary line integral convolution process.

FIG. 12 is a diagram of an exemplary line integral convolution process. Thus, the resolution of the input random texture can determine a resolution of the output. Starting from a random texture, LIC can generate an output texture with noise correlated according to the input vector field.

Figure 13:
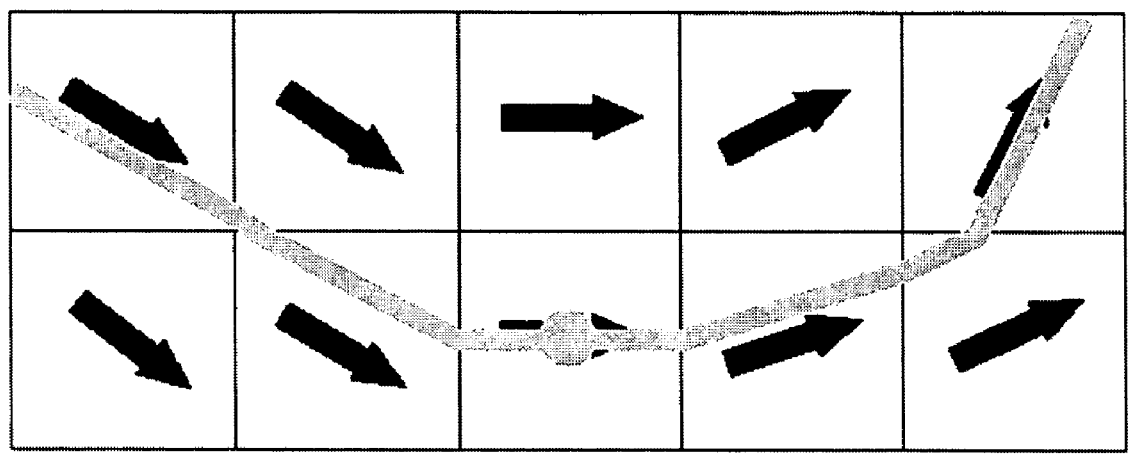
FIG. 13 is a diagram of exemplary streamlines.

To correlate noise, LIC can utilize a concept of streamlines. A streamline can be a line following a flow. In a discrete field, a streamline centered on $x_0$ can be defined as a set of positions $(x_{-n/2}, \ldots, x_{-1}, x_0, x_1, \ldots, x_{n/2})$ computed using the following algorithm:

1. choose $x_0$;
2. compute the forward part recursively until n/2 position are computed: $x_{t+1} = x_t + \epsilon V(x_t)$ where $V(x_t)$ is a vector at location $x_t$;
3. compute the backward part recursively until n/2 position are computed: $x_{t-1} = x_t - \epsilon V(x_t)$ where $V(x_t)$ is a vector at location $x_t$;

FIG. 13 is a diagram of exemplary streamlines.

The goal of LIC can be to correlate the noise by integrating it along streamlines. Thus, two points sharing the same streamline can have many values in common. Algorithm 1 provides a detailed algorithm.

Algorithm 1: LIC in 2d

```
random_image: input noise image
vector_field: input vector field
n: number of streamline steps
output: output 2d image
forall p of output do
    | streamline ← compute_streamline(vector_field, p, n);
    | output[p] ← 0;
    | for i ← −n/2 to n/2 do
    |   | output[p] ← output[p] + random_image[streamline[i]];
    | end
end
```

Where compute_streamline(field, pos, n) is a function returning a vector with n positions of the streamline of field starting at position pos. To give more importance to the streamline steps close to the initial pixel, a distance decreasing weight can be applied to the noise values.

Figure 14:
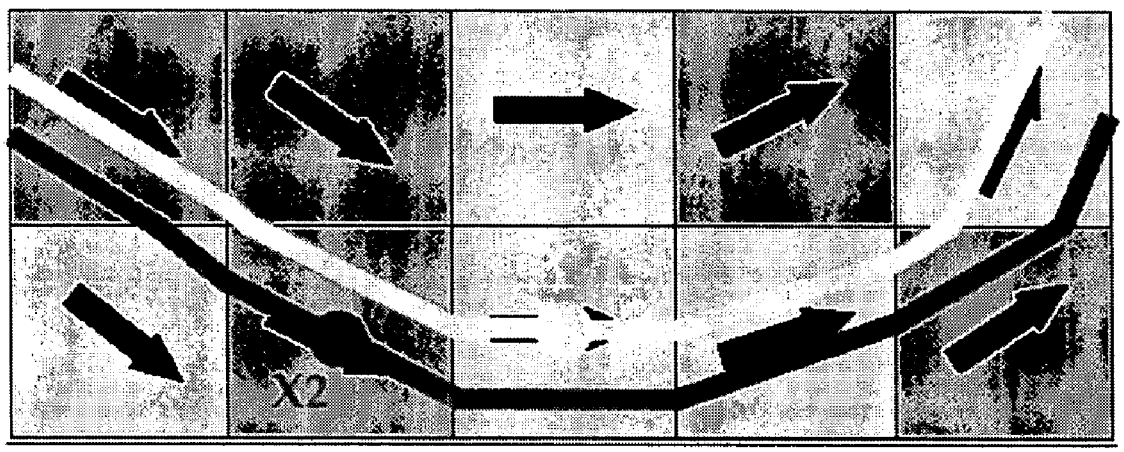
FIG. 14 is a diagram of exemplary streamlines.

FIG. 14 is a diagram of exemplary streamlines correlating noise in the output image according to algorithm 1. Starting from a particular position, a streamline can be computed by recursively by following local directions. The LIC algorithm can provide correlated values for $x_1$ and $x_2$ since the noise summation along their streamlines will share several values.

A pixel-wise step can be a relatively simple and fast algorithm. No interpolation in the vector field might be required if a resolution of a field and a noise image are approximately identical. Actually, the pixel-wise step can be the algorithm used in FIG. 13 and/or FIG. 14. The idea can be to follow each direction until a border of one pixel is reached. A length of a segment in each pixel can vary, so in the LIC algorithm, an actual segment length can weight the contribution of each noise pixel along the streamline.

Euler integration can provide a continuous representation of a vector field. Interpolation (generally linear) can be performed. The principle can be to locally estimate a streamline curvature by a first order derivative, the local vector in the vector field. Then this direction can be followed for a distance ϵ.

Figure 15:
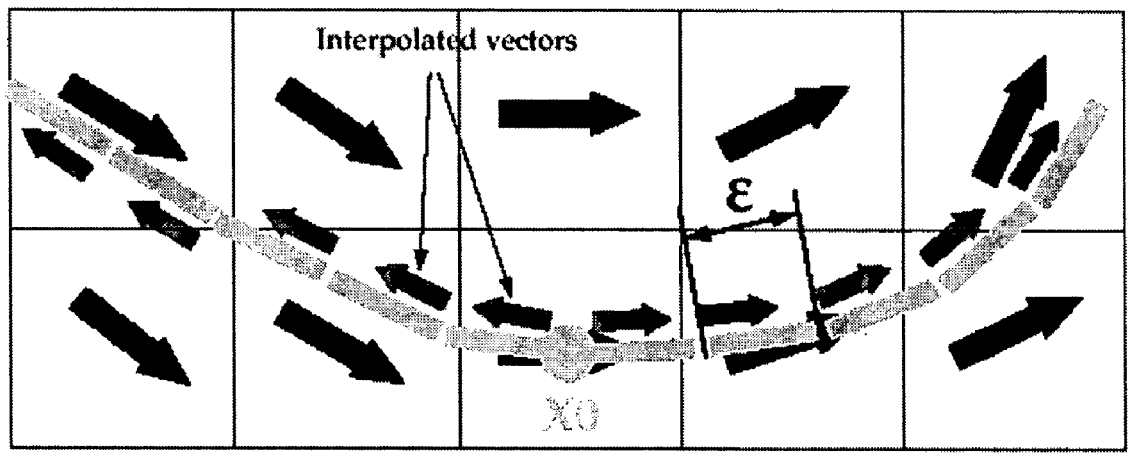
FIG. 15 is a diagram of exemplary streamlines.

FIG. 15 is a diagram of exemplary streamlines. FIG. 15 shows results of a same field as FIG. 14. FIG. 15 shows results obtained via the Euler method for computing streamlines. Each step has a length of ϵ. Directions at each location can be interpolated.

Runge-Kutta integration can be similar to Euler integration. Runge-Kutta integration approximates a local curvature by a fourth order derivative. Thus, Runge-Kutta integration can provide more reliable results than Euler integration. The step size (ϵ) can even be adapted depending of the curvature, the step can be smaller in high curvature regions.

Diffusion can be symmetric, so an actual orientation of vectors might not be relevant. When computing a streamline, a sequence of two vectors with similar directions but opposite orientations might be encountered. This can make a streamline change direction and go backward. To avoid this problem, anti-parallel vectors can be detected using a simple scalar product: v(x) designing the vector at location x, if $v(x_{t+1}) \cdot v(x_t) < 0$ then $v(x_{t+1})$ can be inverted. This way, streamlines can keep a coherent path.

LIC can be a multi-scale algorithm, depending on how dense the noise is in a random input image, the focus can be put on large or small patterns. In addition, the noise probability distribution can be generally Gaussian, but other distributions might give different results.

If an input random image resolution is higher than a vector field resolution, it might be possible to get a good looking output image with the resolution of the random image, just by scaling the vector field using interpolation.

The longer the streamlines, the smoother the result might be, since points sharing streamline portions can have more values in common. However, the shorter the streamline, the faster the computation might be. A length of the streamline can also be determined by an average size of the patterns focused on, if the patterns are small, there might be no point to having long streamlines.

LIC can be utilized to render a 2D slice of the tensor field. A first step can comprise transforming a slice of tensors into a slice of vectors by considering a main eigenvector (the PDD). However, with 3D vectors, which cannot be used directly by LIC in 2D, the vectors can be projected into a plane defined by the slice. To highlight anisotropic regions, an FA mask can be generally applied to the output image. An eigenvector colormap might also be added to show the 3D local directions.

Figure 16:
FIG. 16 is a diagram of exemplary slices of an exemplary brain.

FIG. 16 is a diagram of exemplary slices of an exemplary brain. FIG. 16 illustrates LIC on DT-MRI slices with various parameters and post-processing steps (a), (b), and (c). Post-processing step (a) was without postprocessing, black areas correspond to regions a low FA value, where eigenvectors do not have a real meaning. Post-processing step (b) utilized an FA mask. Post-processing step (c) utilized an FA mask and eigenvector colormap.

Instead of cutting the tensor field into slices, LIC could be computed directly on a 3D vector field, with a 3D random input, and produce a 3D correlated noise. Rendering techniques can display the results. Problems with texture-based methods and volumes can comprise a density of a resulting volume and computational costs. Certain exemplary methods can ameliorate these problems. For example, via masking the volume with an FA value and tuning a volume rendering with well-defined transfer functions, improved results can be obtained. A compromise between 2D and 3D LIC can be surface LIC.

Anisotropic diffusion can be modeled using PDE. A goal of isotropic smoothing can be to reduce the irregularities of an image I. The local irregularity of I at the pixel p can be measured by the norm of its gradient $\|\nabla I\|^2$. Thus, the goal of isotropic smoothing can be to compute:

$$\min_I \int_\Omega \|\nabla I\|^2 d\Omega$$

where $\Omega$ is the domain of I. To find this minimum starting from I, a a gradient descent can be computed, leading to a differential equation for 2D images:

$$\begin{cases} I_{t=0} = I \\ \frac{\partial I}{\partial t} = \Delta I = I_{xx} + I_{yy} = \text{trace}(H) \end{cases} \quad (3.1)$$

where H is the Hessian matrix of I, $I_{xx}$ and $I_{yy}$ the second derivatives of I with respect to x and y, and $\Delta I$ the Laplacian of I (i.e. the sum of its second order derivatives). Notice that trace(H) is equivalent to $\Delta I$. The solution of this PDE at each time step t is the convolution by a normalized Gaussian.

Isotropic smoothing can regularize an image with a same strength in each direction. However, an image can be smoothed while preserving edges. This goal can lead to anisotropic diffusion. Certain exemplary embodiments can smooth in directions that are tangent to the edges. Oriented one-dimensional (1D) Laplacians can be utilized to express anisotropic diffusion. The principle can be to replace an isotropic diffusion PDE resolution $I_{xx}+I_{yy}$ by $\lambda_u I_{uu}+\lambda_v I_{vv}$ with u and v two directions such as $u \perp v$, and $\lambda_u$ and $\lambda_v$ the diffusion coefficients in these two directions. Varying u, v, $\lambda_u$, $\lambda_v$, can make it possible to express an anisotropic directed diffusion ($\lambda_u \neq \lambda_v$). This formulation has some nice mathematical properties. First, $I_{uu}$ and $I_{vv}$ are defined mathematically by: $I_{uu}=u^T H u$ $I_{vv}=v^T H v$ with H the Hessian of I.

As we saw in section 2.4.3, a tensor can be defined by a sum of eigenvectors weighted by the eigenvalues. By choosing:

$$D=\lambda_u u^T u+\lambda_v v^T v$$

we get:

$$I_{uu}+I_{vv}=\text{trace}(DH).$$

This means that by computing a tensor D from the diffusion directions and coefficients u, v, $\lambda_u$, $\lambda_v$, an image can be anisotropically smoothed by calculating trace(DH) at each time step. This can makes a direct parallel with isotropic PDE whose solution was trace(H). The convolution by a Gaussian for isotropic diffusion can be translated into a convolution by a directed Gaussian kernel, defined from D by:

$$G(x, t, D) = \frac{1}{4\pi t} \exp\left(\frac{x^T D^{-1} x}{4t}\right)$$

with t the diffusion time (standard deviation), x the 2D point.

Figure 17:
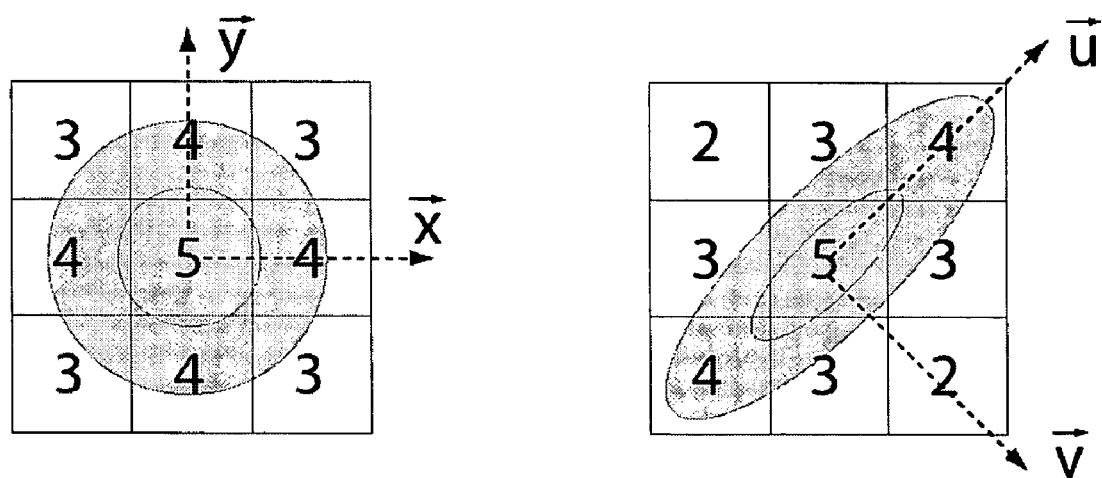
FIG. 17 is a diagram of exemplary isotropic and anisotropic two-dimensional Gaussian kernels.

FIG. 17 is a diagram of exemplary isotropic and anisotropic two-dimensional Gaussian kernels. FIG. 17 gives a graphical view of this Gaussian kernel and summarizes a parallel between the isotropic and the tensor-driven anisotropic worlds. Isotropic and anisotropic 2D Gaussian kernels might not be normalized. These shapes can be defined by a tensor. On the right Gaussian, $\lambda_v < \lambda_u$ gives an ellipsoid shape.

DT-MRI visualization methods based on anisotropic diffusion can be texture-based, as LIC. The idea can be to take a noise image, and smooth it anisotropically, depending on the local tensor information. The process can be then reproduce flow diffusion.

TABLE I

| PDE solution | Isotropic | Anisotropic |
|---|---|---|
| Expanded | $I_{xx} + I_{yy}$ | $\lambda_u I_{uu} + \lambda_v I_{vv}$ |
| Trace-based | trace(H) | trace(DH) |
| Convolution kernel | $G(x, t) = \frac{1}{4\pi t}\exp\left(\frac{x^T x}{4t}\right)$ | $G(x, t, D) = \frac{1}{4\pi t}\exp\left(\frac{x^T D^{-1} x}{4t}\right)$ |

Figure 18:
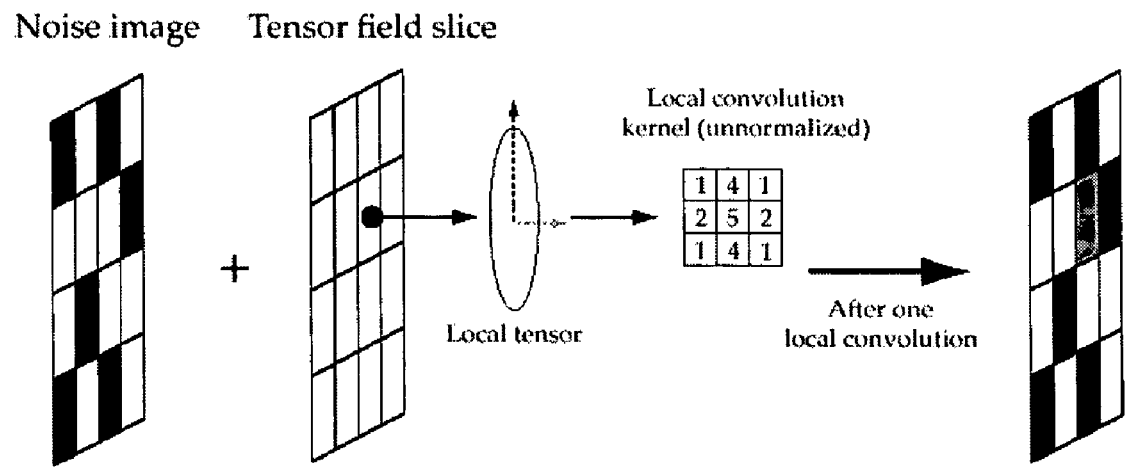
FIG. 18 is a diagram of an exemplary diffusion model.

FIG. 18 is a diagram of an exemplary diffusion model. Certain exemplary embodiments can provide an image using directions and a shape defined by a tensor. An application to texture-based DT-MRI visualization can be relatively straightforward. For each pixel in a noise texture, a diffusion tensor can be diffused locally in the tensor field. This can be illustrated by FIG. 18, which illustrates PDE diffusion at one location. This process can be repeated for each pixel to give a next step in a noise image.

Local diffusion can be implemented either by using a finite difference scheme with trace(DH) or by using local filtering with the convolution by an oriented Gaussian kernel. Some advantages of convolution can comprise:

- the kernel size can be chosen, thereby taking into account more neighbors;
- by using normalized Gaussian, a global image energy can be preserved; and/or
- it can result in more precise and detailed images; etc.

These advantages can have a performance cost, but with some implementation tricks it might not be significant. The process can be detailed in Algorithm 2. Performance can be improved with a convolution kernel buffer. Indeed, the tensor field might not change at each iteration, and the convolution kernels might depend on corresponding tensors. So instead of calculating each convolution kernel at each step, one can store all or some of them depending on the available memory. For 2D slices, a memory overhead can be acceptable.

---

Algorithm 2: PDE in 2d.

```
random_image: input 2d noise image
vector_field: input vector field
n: number of diffusion steps
t: diffusion time per step
kernel: convolution kernel structure
output: output 2d image output ← random_image;
while number or steps < n do
| forall p of output do
| |  D ← vector_field[p];
| |  forall v = (x, y) of kernel do
| |  |  kernel[x][y] ← (1/(4πt)) exp(vᵀD⁻¹v / 4t);
| |  end
| |  tmp_output[p] = convolution(output, kernel, p);
| end
| output = tmp_output;
end
```

---

PDE diffusion can be a multi-scale process. By computing only a few iterations, only a few details might be rendered. With more iterations, more of a global structure can be captured.

A diffusion time per step can be chosen to be the highest time ensuring numerical stability. A diffusion time that is too low can decrease performance, whereas a diffusion time that is too high can yield inaccurate results.

In determining a convolution kernel size, taking more neighbors into account can increase a result's accuracy. However, taking more neighbors into account can increase computation time and memory (for kernel buffering). In practice, 5×5 kernels can be a compromise.

Using diffusion tensors extracted from the tensor field might lead to over-smoothed results. Certain exemplary embodiments can replace an actual tensor by:

$$D = uu^T + g(FA)(Id - uu^T)$$

with g a decreasing function, u the principal diffusion direction and FA the fractional anisotropy. The idea can be to focus on the main direction, and to set the degree of anisotropy depending on the FA. Thus, this function can smooth isotropically regions with low FA. In certain exemplary embodiments, an over-smoothed general result image can result. In certain exemplary embodiments, a simpler function can be utilized:

$$D = h(FA) * uu^T$$

with h an increasing function. This way, low FA regions can remain noisy, and high FA regions can be smoothed with a strength depending on their degree of anisotropy. An example of satisfying h can be $h(FA) = FA^2$.

Figure 19:
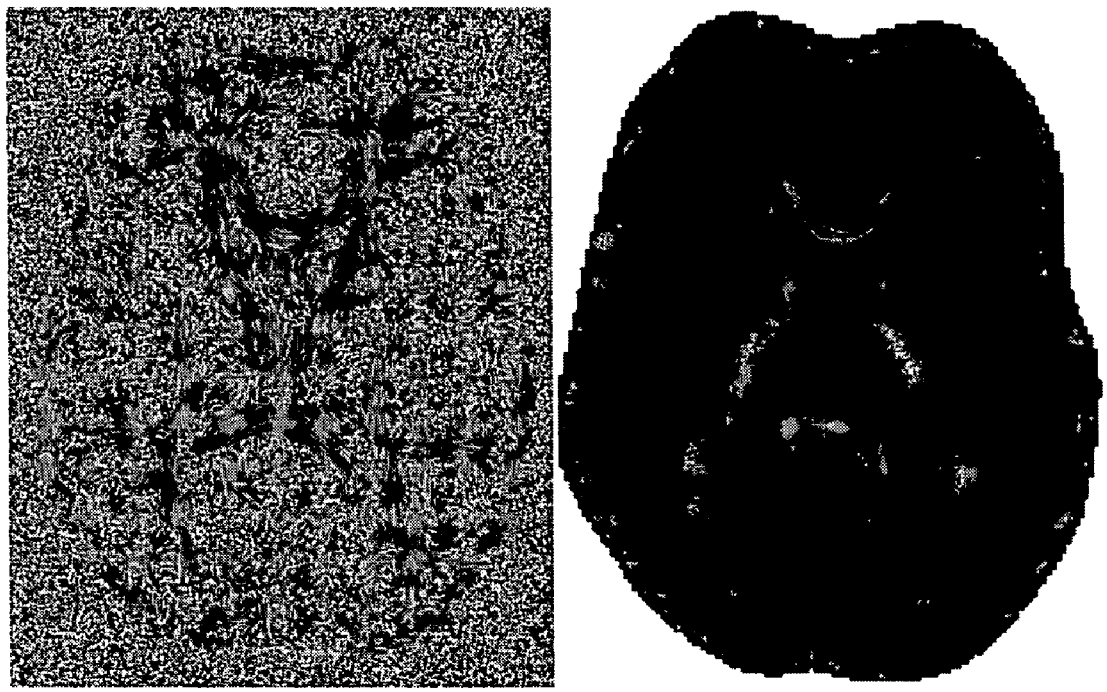
FIG. 19 is a diagram of exemplary images determined from an exemplary brain.

FIG. 19 is a diagram of exemplary images determined from an exemplary brain, which shows results obtained with DT-MRI slices. The portion on the left illustrates diffusion by convolution after 15 steps. The portion on the right illustrates a rendering obtained via an FA mask and eigenvector colormap postprocessing.

The PDE framework can be flexible. In addition to global visualization, certain exemplary embodiments can render information related to local brain connectivity, that is, starting from a seed point or a seed region, determine which regions can be reached. This can be done within the same framework as above. Instead of using a random input texture, a blank texture can be utilized with one seed point or seed region with some intensity. Then, applying the diffusion process, an intensity can spread into the regions connected to the seeds. Certain exemplary embodiments can utilize anisotropic kernel smoothing.

Figure 20:
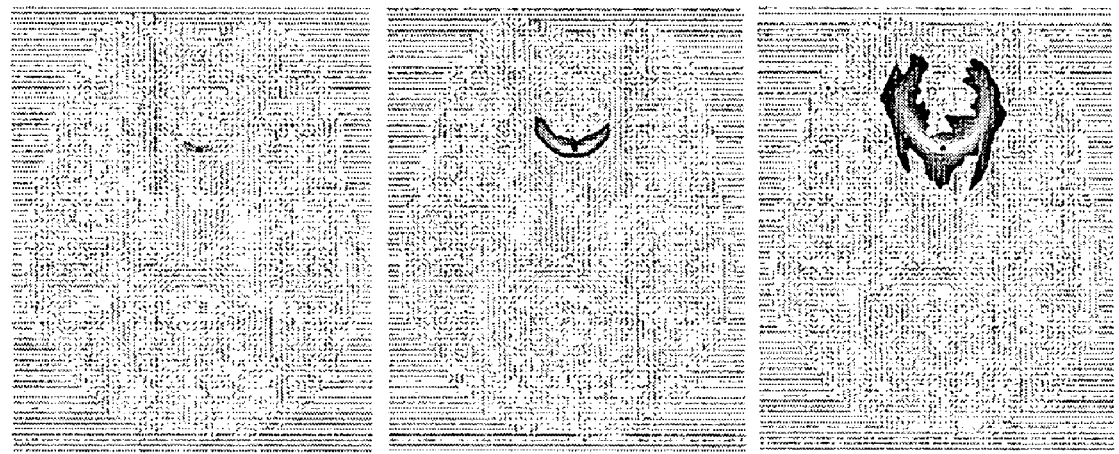
FIG. 20 is a diagram of exemplary images determined via modeling diffusion from a seed voxel.

FIG. 20 is a diagram of exemplary images determined via modeling diffusion from a seed voxel, which provides results of connectivity analysis on a brain slice. Since the influence of the seed point's intensity exponentially decreases with the distance toward a destination pixel, a log scale was applied to visualize the results. FIG. 20 illustrates diffusion of one seed point after 5, 15 and 100 iterations. The background can be composed of segment glyphs corresponding to the eigenvectors of the tensor field.

PDE based diffusion might not be restricted to 2D slices of DT-MRI data. However, like LIC, the PDE approach can be texture-based, and suffer from similar visualization problems. Computation time can be also intractable for a whole volume. But whereas LIC can utilize a full texture, just set one or several seed points and can yield a map measure. This way, the diffusion process can be greatly simplified by focusing on areas around seed points (everywhere else the intensity will be zero).

The PDE framework gives at least comparable results with LIC. The PDE framework can have several advantages:
flexibility: more parameters can be set, it can be used to compute connectivity maps;
accuracy: the whole tensor information might be taken into account;
performance: if the convolution kernels can be buffered, PDE-based approach can be faster than LIC;
partial applicability in 3D.

On the other hand, by computing streamlines, LIC can provide a representation closer to the aspect of fibers.

Diffusion tensors can provide clues about the geometrical organization of the brain, making it partially possible to reconstruct fiber paths. Connectivity in the brain can be effected via axonal fibers. These fibers can be surrounded by myelin membranes, which can restrict water diffusion to a direction of the fibers. The goal of fiber tracking can be to follow a fiber, starting from a given seed point. Actually tracking individual fibers can be difficult due to their microscopic size, so only bundles of parallel fibers might be tracked. Fiber tracking from DT-MRI data can be difficult. No validation method for tracking results is known to be available on real datasets. However, qualitative judgments can be made if the results are plausible considering known anatomy.

Certain exemplary embodiments can track fibers using methods that are deterministic or probabilistic, local or global, etc. An intuitive and straight forward method to track fibers starting from one seed point can comprise recursively following a principal diffusion direction. This can be similar to a streamlines computation:

$$\begin{cases} d(t) = e_1(x(t)) \\ x(t+1) = x(t) + \Delta t \cdot d(t) \end{cases}$$

with x(t) the position at step t, $e_1(p)$ the main eigenvector of the tensor at location p and $\Delta t$ the step size. A drawback of a deterministic method can be an inability to handle the uncertainty due to branching or partial volume effects. The main eigenvector might not be relevant for spherical or planar tensors, and only one direction will be chosen in case of branching (generally not even one of the branches). In addition, once a wrong direction can be chosen, errors can propagate and can be cumulative.

Certain exemplary embodiments can comprise a fast marching algorithm. The fast marching algorithm can propagate a front from a seed point. The front evolution and speed can depend on tensor information and when a point can be reached, the arrival date can be stored. After propagation completion, fiber paths can be reconstructed with a simple shortest path algorithm through the arrival dates. The fast marching algorithm can handle branching and uncertainties since the fast marching front can split. On the other hand, only the main eigenvector of each tensor might be considered, so crossing fibers or partial volume effects can slow down the algorithm and introduce inaccuracies, which may lead to a wrong shortest path. Certain exemplary embodiments can start from one seed point and propagate from the seed point in the whole 3D tensor field. As a result, many shortest paths can be computed. This might be unacceptably slow for interactive fiber tracking.

To handle local uncertainties, certain exemplary embodiments can utilize a global optimization. Certain exemplary embodiments can utilize Markov random fields to obtain a global regularization and make fiber tracking tractable.

Certain exemplary embodiments can adapt linear state-space models to fiber tracking. Kalman filters can be used to track an object when noisy measurements are available. The object evolution direction can be estimated in two steps:
a predictive step, using a priori evolution information; and
a correction step, taking into account the actual measurement.

Certain exemplary embodiments can comprise defining each direction measurement as the main eigenvector, and the a priori predicted direction as being the same as the previous one. This can result in regularity of fiber paths. Kalman filters can take into account two kind of noise: prediction noise and measurement noise. Prediction noise can be set according to the tensor, an isotropic tensor can lead to a large noise. In some sense, the whole tensor information can be used. However, Kalman filters can have limitations, such as:
evolution might be linear i.e. $x_{t+1}=f(x_t)+$noise with linear; and/or
noises might be Gaussian, etc.

This might not be the case with real data. In addition, this model might not handle branching or crossing fibers well.

Since fiber tracking can be ill-posed with real data, stochastic methods can be used instead of deterministic ones. Certain exemplary embodiments can comprise a random walk technique, with various tensor data preprocessing. The idea can be to start several tracks from one seed point, driven by probabilistic criteria. This makes it possible to handle uncertainty, such as branching: some of the tracks will choose the first branch, others will choose the second one. Certain approaches can suffer from limitations. First, when branching is involved, the density of tracks can be divided by two. So after a few ambiguous points, only a few tracks might still continue on each path. Then, some paths might end up in uninteresting areas (because of misleading isotropic tensors), and this can reduce the proportion of promising tracks. Certain exemplary embodiments can comprise Kalman filters. Particle filters can handle non-linear and non-Gaussian noise, thereby being much more flexible. Particle filters can belong to a random walk family of Monte-Carlo methods. Certain exemplary embodiments can comprise particle filters for fiber tracking.

Particle filters, also called sequential importance sampling resampling or bootstrap filters can be used to track objects in a noisy environment. The goal of the filter can be to estimate an actual position of an object from noisy measurements. A model can comprise two parts: an evolution model and a measurement process. The evolution model can be described as:

$$x_t = f(x_{t-1}, n_f(t))$$

where $x_t$ is the position at time t, f an arbitrary function, and $n_f(t)$ the noise at time t. This is a first order Markovian model, the position at time t can depend on the position at time t−1. The values for f and $n_f(t)$ might be known. In addition to this noisy evolution model, noisy measurements can be available (from sensors for example):

$$z_t = h(x_t, n_h(t))$$

with $z_t$ the measurement at time t, h an arbitrary function and $n_h(t)$ the noise associated to the measurement at time t.

A goal of particle filters can be to estimate the probability $p(x_0, \ldots, x_t | z_1, \ldots, z_t)$, that is, the probability of one path after having observed the measurements. It can be difficult to express this probability analytically. To estimate the probability, Monte-Carlo methods can draw a set of discreet samples following the distribution p. This can be done recursively by drawing new positions at each time step from $p(x_t|x_{t-1})*p(z_t|x_t)$. The value $x_{0:k} = x_0, x_1, \ldots, x_k$. The result after k time steps can be a group $\{x_{0:k}^i\} i=1 \ldots N$ of N paths of length k, each path $x_{0:k}^i$ following the distribution of $p(x_{1:k}^i|z_1, z_2, \ldots, z_k)$. The actual process can be more complex than this, involving importance sampling. A measurement and evolution process can be derived from the Kalman filters approach. The measurement used with Kalman filters can be the main eigenvector of the tensor at the current location. This means, for each sample $x_{0:k}^i$, the measurement z(k) would be the PDD at location $x_k^i$. This might not be compatible with classical particle filters models for tracking, since the measurements are different for each sample. The samples might not estimate a single tracking process. This means that known measurement models for fiber tracking might not be usable within a Monte-Carlo approach. However, particle filters can be a general framework, not limited to state-space models with measurements.

Certain exemplary embodiments comprise a state-space model, but without measurements. The problem of tracking can be seen as finding the path $x_{0:k}$, which maximizes a probability $p(x_0, x_1, \ldots, x_k)$. In practice, this probability can be complex, depending of the tensors the path encounters, on regularity criteria, etc. Thus, it can be not possible to find analytically arg max $p(x_0, \ldots, x_k)$. This can be a point of utility of Monte-Carlo methods. Since we cannot express p analytically, let's suppose we could draw N+1 samples $\{x^i\}_{i=0 \ldots N}$ from it. Then p can be estimated by:

$$p(x) = \frac{1}{N}\sum_{i=0}^{N} \delta(x^i)$$

with $\delta(x)$ the delta-dirac mass function at position x. Then arg max p(x) can be simply arg max $\{p(x^i)\}_{i=0 \ldots N}$, the sample with the best probability. It can be shown that:

$$\lim_{N\to\infty} \mathrm{argmax}\{p(x^i)\}_{i=0 \ldots N} = \mathrm{argmax}\, p(x)$$

In practice, we can obtain a good estimation with a reasonable N. The difficulty can be now to draw samples from p. A key point can be that p can be determined, but this does not mean we can draw samples from it.

Importance sampling can be a general technique to draw a set of samples from a non obvious probability distribution p. Certain exemplary embodiments can draw samples from a simpler probability function q, called the importance density, and then to compensate for the difference between q and p by associating a weight to each sample. A value of q can be chosen to support at least the domain of p, and samples can be obtained from it (typically some kind of Gaussian distribution). If a sample x is drawn from q there are several possibilities:

p(x)=q(x): x can be a good sample for p p(x)>q(x): this means that among the samples drawn from q, the number of samples in the region of x might be underestimated with respect to p p(x)<q(x): here x had more chances to be drawn by q than by p, the region of x might be overestimated.

To get a proper set of samples from p, importance sampling can associate a weight to each sample to compensate the over or underestimation of the local density. The set of samples becomes:

$$\{x^i, w^j\}_{i=0 \ldots N}$$

$$w^j = \frac{w^j_{unnormalized}}{\sum_{i=0}^{N} w^j_{unnormalized}} \text{ with}$$

$$w^j_{unnormalized} = \frac{p(x^j)}{q(x^j)}$$

Now p can be approximated from the set of samples with normalized weights by:

$$p(x) = \sum_{i=0}^{N} w^i \times \delta(x^i)$$

Figure 21:
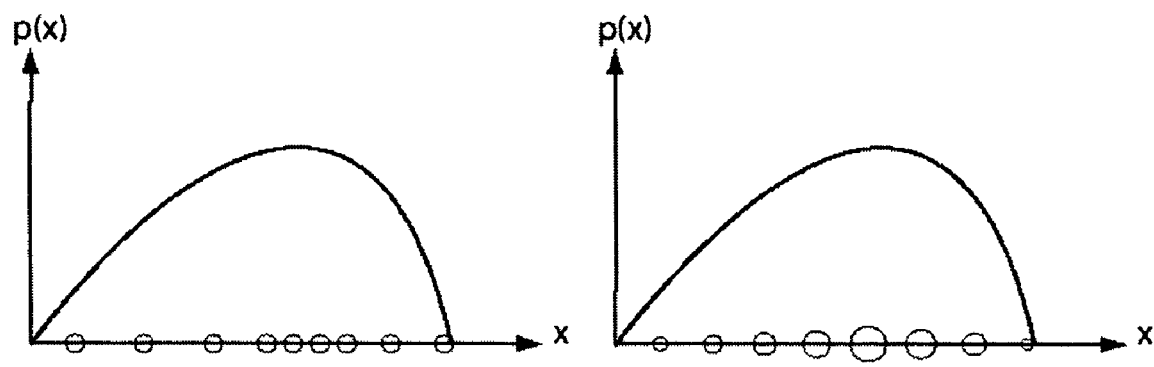
FIG. 21 is a diagram of exemplary probability models.

FIG. 21 is a diagram of exemplary probability models, which illustrates the role of the weights. On the left, a set of samples is directly drawn from p. On the right, a set of samples drawn from an uniform distribution q. To compensate the over and underestimations, a weight (the radius of the sample) can be assigned to each sample.

If we suppose the model to be first order Markovian, p can be rewritten recursively as:

$$p(x_0, x_1, \ldots, x_k) = \quad (4.1)$$

$$p(x_k|x_0, x_1, \ldots, x_{k-1}) \times p(x_0, x_1, \ldots, x_{k-1}) = p(x_k|x_{k-1}) \times$$

$$p(x_{k-1}|x_{k-2}) \times \ldots \times p(x_1|x_0) \times p(x_0) = p(x_0) \times \prod_{t=1}^{k} p(x_t|x_{t-1})$$

If it is possible to draw samples from $p(x_t|x_{t-1})$, samples of $p(x_0, x_1, \ldots, x_k)$ can be obtained recursively. The problem (simpler) can be now to sample from $p(x_t|x_{t-1})$.

The expression $p(x_t|x_{t-1})$ can be the transition probability to reach position $x_t$ from position $x_{t-1}$. This model can be flexible since only the transition probability needs to be provided, and we will see later that it can be arbitrarily complex. For a fiber problem, it can be defined using 3 terms:

$$p(x_t|x_{t-1}) = p_{tensor}(x_t|x_{t-1}) \times p_{reg}(x_t|x_{t-1}) \times p_{fa}(x_t|x_{t-1})$$

with $$p_{tensor}(x_t|x_{t-1}) = \frac{1}{(2\pi)^{3/2}} \exp\left(-\frac{1}{2}(x_t - x_{t-1})^T D(x_{t-1})^{-1} (x_t - x_{t-1})\right)$$

with D(x) the normalized tensor at location x. An evaluation of $p_{tensor}$ can provide an estimation of how likely can be the new direction $x_t - x_{t-1}$ with respect to $D(x_{t-1})$. An evaluation of $p_{reg}$ can be derived from the Euclidean distance between $x_{t-1} - x_{t-2}$ and $x_t - x_{t-1}$ (the direction change) to avoid wiggly paths. An evaluation of $p_{fa}$ can be computed from the fractional anisotropy at location $x_t$ to promote destinations with a high anisotropy. This can be one proposition for $p(x_t|x_{t-1})$, many others are possible. Since it can be possible to draw from $p_{tensor}$ (a multivariate Gaussian), and its support can be bigger than the support of p, we can use importance sampling to draw a set of properly weighted samples from $p(x_t|x_{t-1})$, with $q = p_{tensor}$. Finally, the recursive equations to estimate both the probability of one path (one sample) $p(x_{0:t}^i)$ and its weight $w_{0:t}^i$ at time t can be expressed as:

$$p(x_{0:t}^i) = p(x_t^i|x_{t-1}^i) p(x_{0:t-1}^i)$$

and $$w_{0:t}^i = \frac{p(x_{0:t}^i)}{p_{tensor}(x_{0:t}^i)}$$

$$= \frac{p(x_t^i|x_{t-1}^i) p(x_{0:t-1}^i)}{p_{tensor}(x_t^i|x_{t-1}^i) p_{tensor}(x_{0:t-1}^i)}$$

$$= \frac{p(x_t^i|x_{t-1}^i)}{p_{tensor}(x_t^i|x_{t-1}^i)} w_{0:t-1}^i$$

Using these equations, we can maintain a collection of samples $\{x_{0:t}^i, w_{0:t}^i, p(x_{0:t}^i)\} i=0\ldots N$ efficiently. At each time step, the best path can be the sample with the highest probability. Algorithm 3 summarizes the tracking process.

---

Algorithm 3: Sequential Importance Sampling for fiber tracking.

--- tensor_field: input tensor field
$x_0$: seed point
output: the best path
while tracking not finished do
  foreach sample $x_{0:t}^i$ do
    dt ← draw_direction_from_p_tensor(tensor_field[$x_t^i$]);
    $x_{t+1}^i \leftarrow x_t^i + dt$;
    $p(x_{0:t+1}^i) \leftarrow p(x_{0:t}^i) p(x_{t+1}^i|x_t^i)$;
    $\omega_{0:t+1}^i \leftarrow \omega_{0:t}^i \frac{p(x_{t+1}^i|x_t^i)}{p_{tensor}(x_{t+1}^i|x_t^i)}$;
  end
  normalize_weights( );
  t ← t + 1;
end
output ← arg max $p(x_{0:t}^i)$;

---

In the previous section, the importance density $q = p_{tensor}$ was chosen. This might not be the only possibility. If the local tensor is, say, isotropic because of crossing fibers, the samples generated by q can be approximately equally distributed in 3D space. To ensure that some new samples will be generated in the continuity of the previous direction (direction changes are generally continuous), a sample might not be drawn from the probability defined by the local tensor. Instead, a new tensor can be computed, taking into account not only the current tensor, but also the previous direction.

$$D_{reg} = fa \times D + (1-fa) \times d_{t-1}^T d_{t-1}$$

with D the local tensor, a the coefficient of regularity, $d_{t-1}$ the previous path direction and fa the local fractional anisotropy. This ensures that when the tensor can be isotropic, directions close to the previous one will be privileged, whereas in highly anisotropic regions a bigger importance can be given to tensorial information. This importance density can be finally taking into account a part of the $p_{reg}$ term of p. Finally, generating samples from a tensor $D_{reg}$ can comprise drawing samples from a 3D Gaussian using $D_{reg}$ as the covariance matrix.

Since the samples can be drawn from an importance density $p_{tensor}$, which does not take, into account regularity or anisotropy criterion, some samples might be generated in areas with a very low probability in the sense of p.

Figure 22:
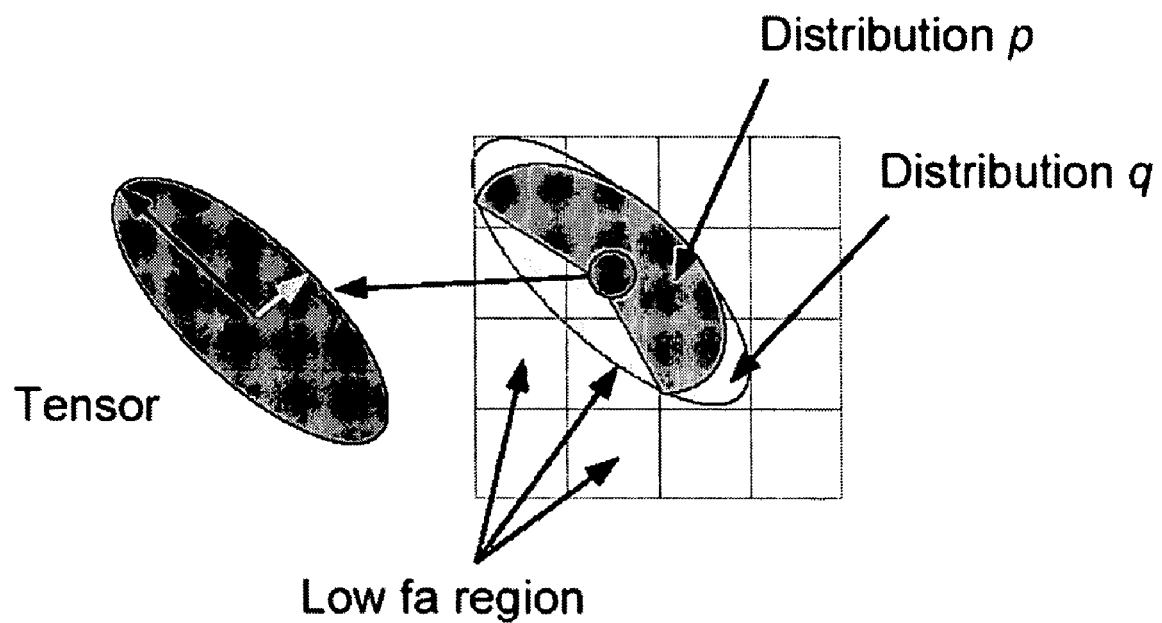
FIG. 22 is a diagram of exemplary tensors.

FIG. 22 is a diagram of exemplary tensors, which illustrates that drawing from q, samples can be generated into the low FA region, only restricted by p. Small weights can be associated with certain samples. Thus, after a few steps, degeneracy may occur: most samples might end up with low weights (each overestimation), and a few others might get very important weights (through weight normalization). The goal of the resampling step can be to avoid such degeneracy.

Degeneracy can be evaluated via an equation:

$$\widehat{N_{eff}} = \frac{1}{\sum_{i=0}^{N} (w_{0:k}^i)^2}$$

The expression $\widehat{N_{eff}}$ can be related to the variance of the weights, a very low $\widehat{N_{eff}}$ related to a strong degeneracy of the weights. In such a case, a resampling algorithm can be used to duplicate samples with high weights and remove samples with low weights. A biased wheel algorithm with the weight as the probability of being drawn can perform well.

Uncertainties can be handled by generating samples for possible areas. Thus, branching can be handled, if a branching point between two fibers is met, the samples can split into two equal parts (in probability). This can lead to a drop of particle density in each branch. After a few branching point, the number of samples might be seriously decreased, and some branches might be abandoned after a few resampling steps. To cope with these problems, a clustering algorithm can be utilized to detect separated groups of samples, and start several distinct tracking with N samples in each branch by duplicating good samples.

Figure 23:
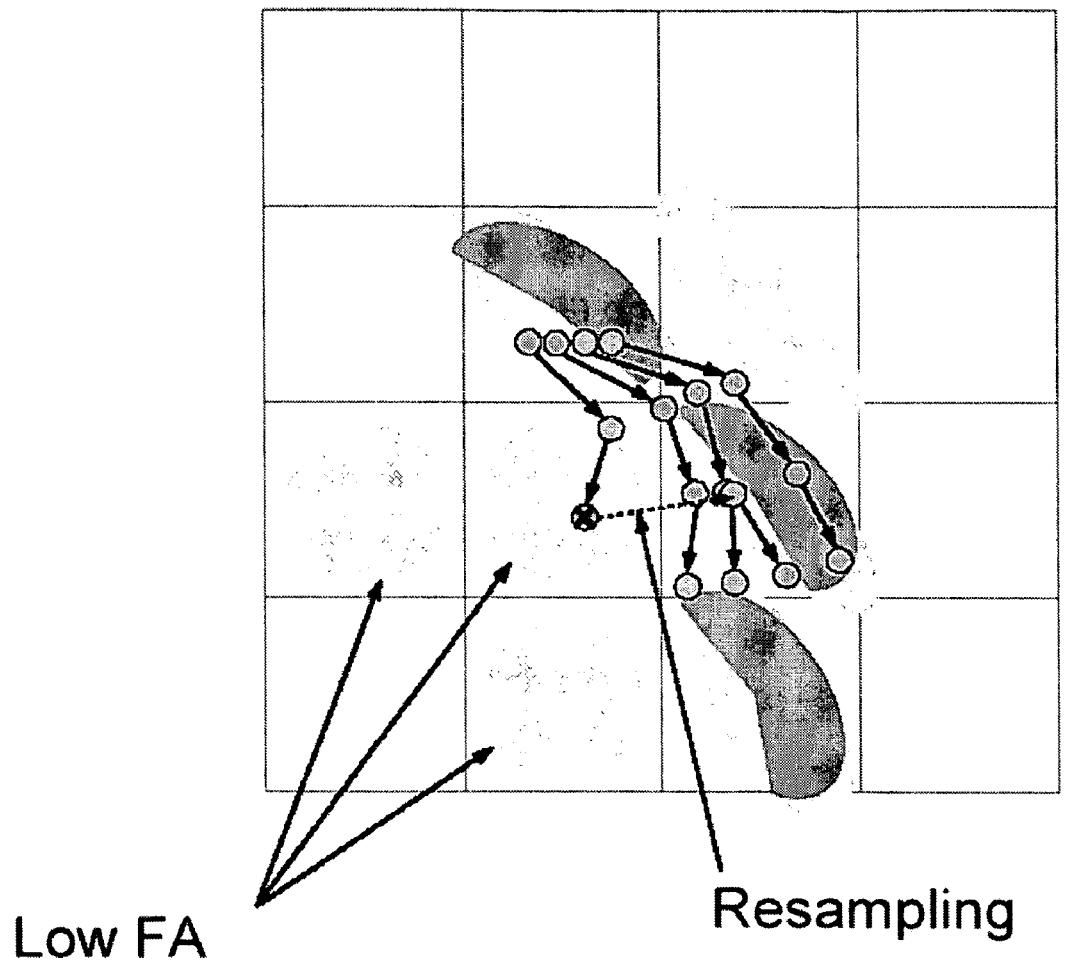
FIG. 23 is a diagram of exemplary tensors.

FIG. 23 is a diagram of exemplary tensors, which comprises a sample generated in a low probability region, and accumulated over estimations compared to others due to high FA. A resampling step removed the sample and duplicated a good sample instead. This can be close to multi-modal tracking in classical particle filters theory.

Figure 24:
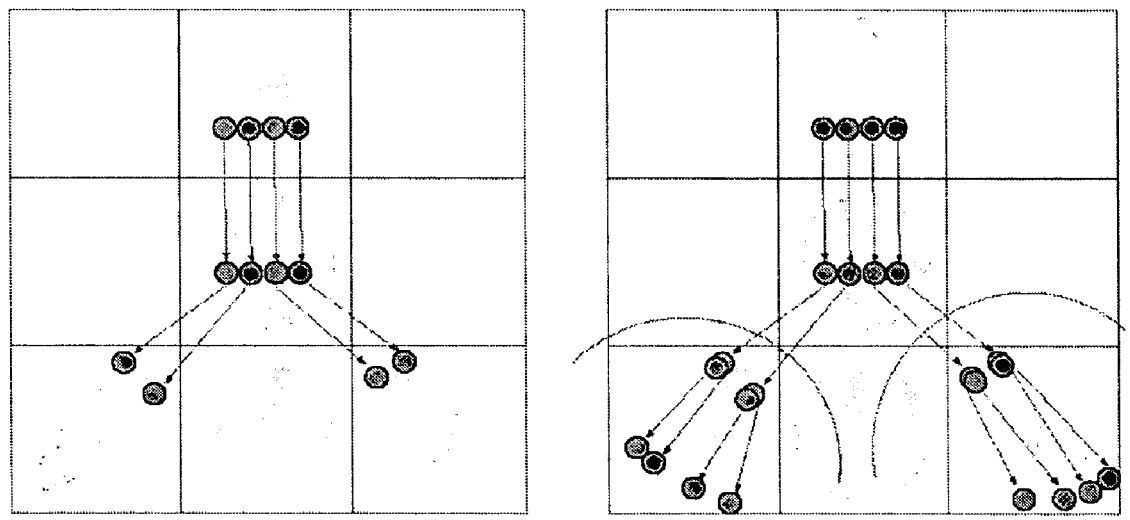
FIG. 24 is a diagram of exemplary modeled fibers.

FIG. 24 is a diagram of exemplary modeled fibers, which illustrates the principle of the approach. The left portion illustrates that without clustering a algorithm, particle density can be divided when branching occurs. The right portion illustrates that one distinct tracking process can be created for each branch. Missing particles can be added by duplicating existing ones. The clustering algorithm can be fast since it will be applied almost at every step of each tracking. A number of groups can be unknown, a branching or crossing point might lead to more than two paths. An algorithm close to k-means, but with an ability to dynamically create classes was developed. The method is presented as Algorithm 4. Algorithm 4 takes advantage of the knowledge we have about the distance between samples, we know for example that a distance of five voxels can be too big for two particles following the same fibers.

---

Algorithm 4: Clustering of particles.

particles: samples to cluster
max_distance: maximal distance between two particles in the same cluster
centers: the cluster centroids
centers ← pick_one_particle_from(particles);
while centers has changed do
| // Assign particles to centroids;
| forall p in particles do
| | closest_center ← arg min$_{center \in centers}$ distance(p, center);
| | if distance(p, closest_center) < max_distance then
| | | cluster(p) ← closest_center;
| | else
| | | // Create a new cluster for this particle;
| | | centers ← centers ∪ p;
| | | cluster(p) ← p;
| | end
| end
| // Update centroids;
| forall center in centers do
| | center ← mean of all particles p such as cluster(p) = center;
| end
end
// Remove small centers;
| forall center in centers do
| if number of particles such as cluster(p) = center < min_cluster_size
| then
| | centers ← centers \ center;
| | reassign particles p such as cluster(p) = center;
| end
end
// Update centroids;
forall center in centers do
| center ← mean of all particles p such as cluster(p) = center;
end

---

Figure 25:
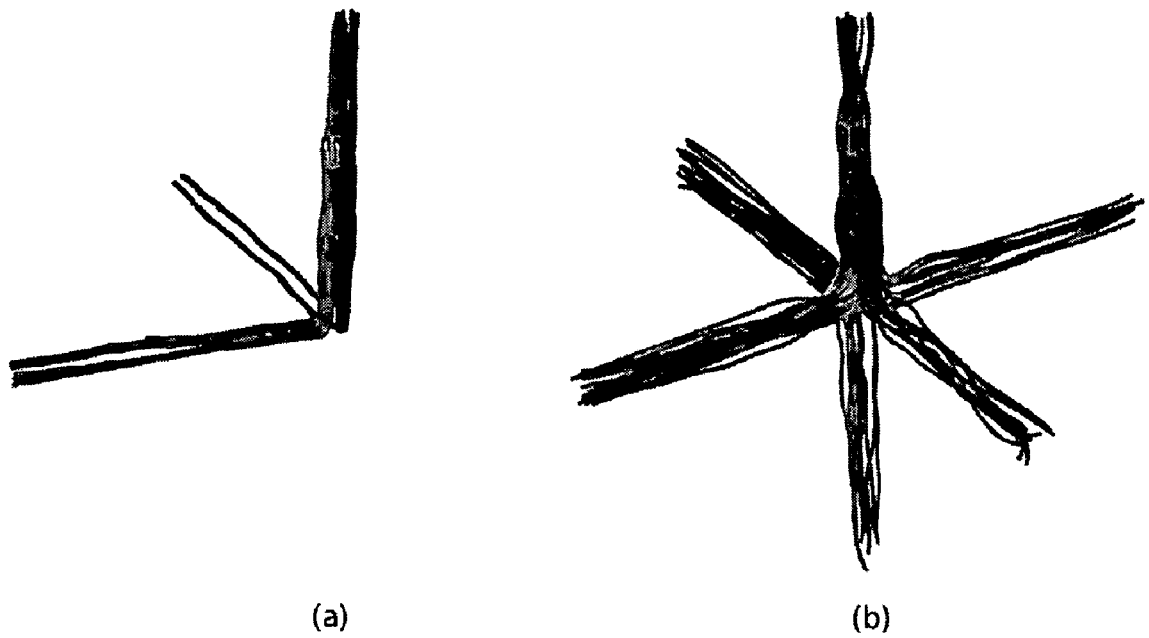
FIG. 25 is a diagram of exemplary modeled fibers.

FIG. 25 is a diagram of exemplary modeled fibers created via Algorithm 4. This simple algorithm can perform quite well. The exemplary modeled fibers (a) illustrate PDD tracking on a generated noisy cross-shaped tensor field. Several tracking processes were started from a seed region. Only two branches were detected. The density in each branch was reduced. The exemplary modeled fibers (b) illustrate SISR tracking with branching based on an clustering algorithm. All branches were equally tracked, and the density was not reduced.

Two criterions can be used to determine if a path should be stopped:
the FA average of the few last positions, if the FA is too low for a long time, it means we are tracking in a gray matter region, there might be no more fibers to track; and
the curvature can be too high and real fibers do not bend very sharply.

If one of these conditions can be verified for one particle, its weight can be set to zero and the resampling step can duplicate a still living particle to replace it. When all particles are stopped in a group, tracking can be stopped.

Finally a best path can be extracted from each particle group, and a goal can be to visualize these paths. A potential representation can be tubes. Several postprocessing steps can be applied to tubes, such as:
the radius of the tubes can be modulated by the FA in each point;
the color of the tubes can be encoded following the main direction (like eigenvector colormaps); and/or
tubes can be smoothed a posteriori using nurbs regression; etc.

Figure 26:
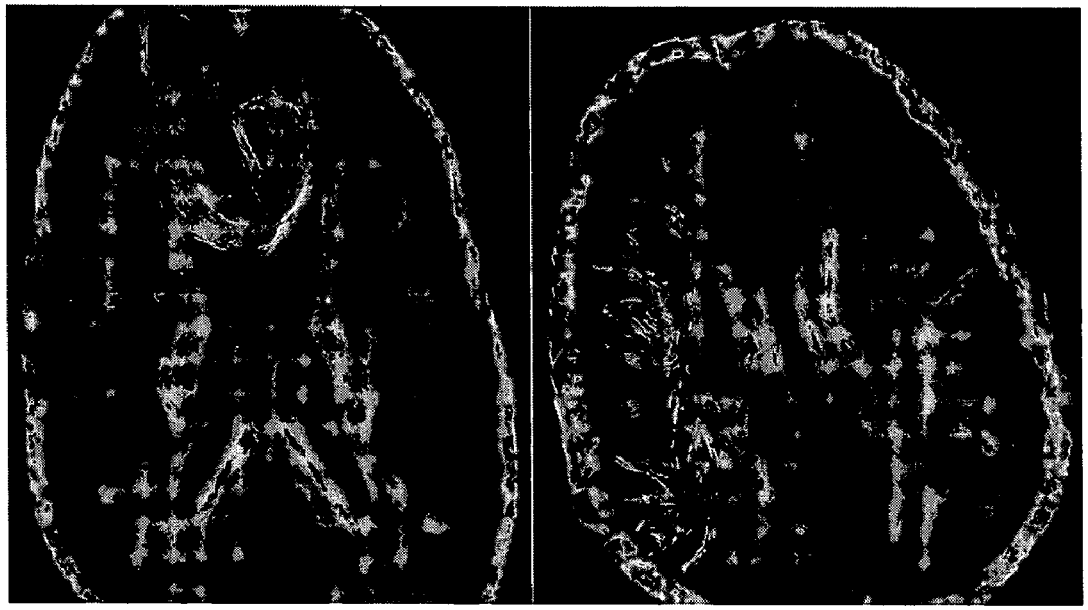
FIG. 26 is a diagram of exemplary modeled fibers in exemplary slices of an exemplary brain.

FIG. 26 is a diagram of exemplary modeled fibers in exemplary slices of an exemplary brain, which illustrate results in good-looking fiber-like shapes utilizing this method.

This method has several potential limitations compared to global methods. First, it might not be deterministic. Two consequent runs might not give the same fibers. The symmetry test might not be validated either (checking that if one point d can be reached by a fiber starting at o, o can be also reached by tracking from d). In addition, like all tracking methods, it might not be possible to clinically validate it, even if the results in the human brain are compatible with known anatomy. However, SISR can provide a flexible yet powerful framework for interactive fiber tracking. Uncertainties can be intrinsically handled. A special process can be even possible for branching fibers, allowing long paths tracking in complex regions. While slower than simple PDD tracking, the method remains local and fast enough for interactive tracking, which might not be possible with global approaches. The method can be subject to improvements, such as:
more probability terms could be added, taking into account more a priori information;
the tensor probability could also consider the Rician nature of the noise; and/or
the clustering algorithm could be improved to detect fuzzy clusters, which appear in really noisy datasets; etc.

Figure 27:
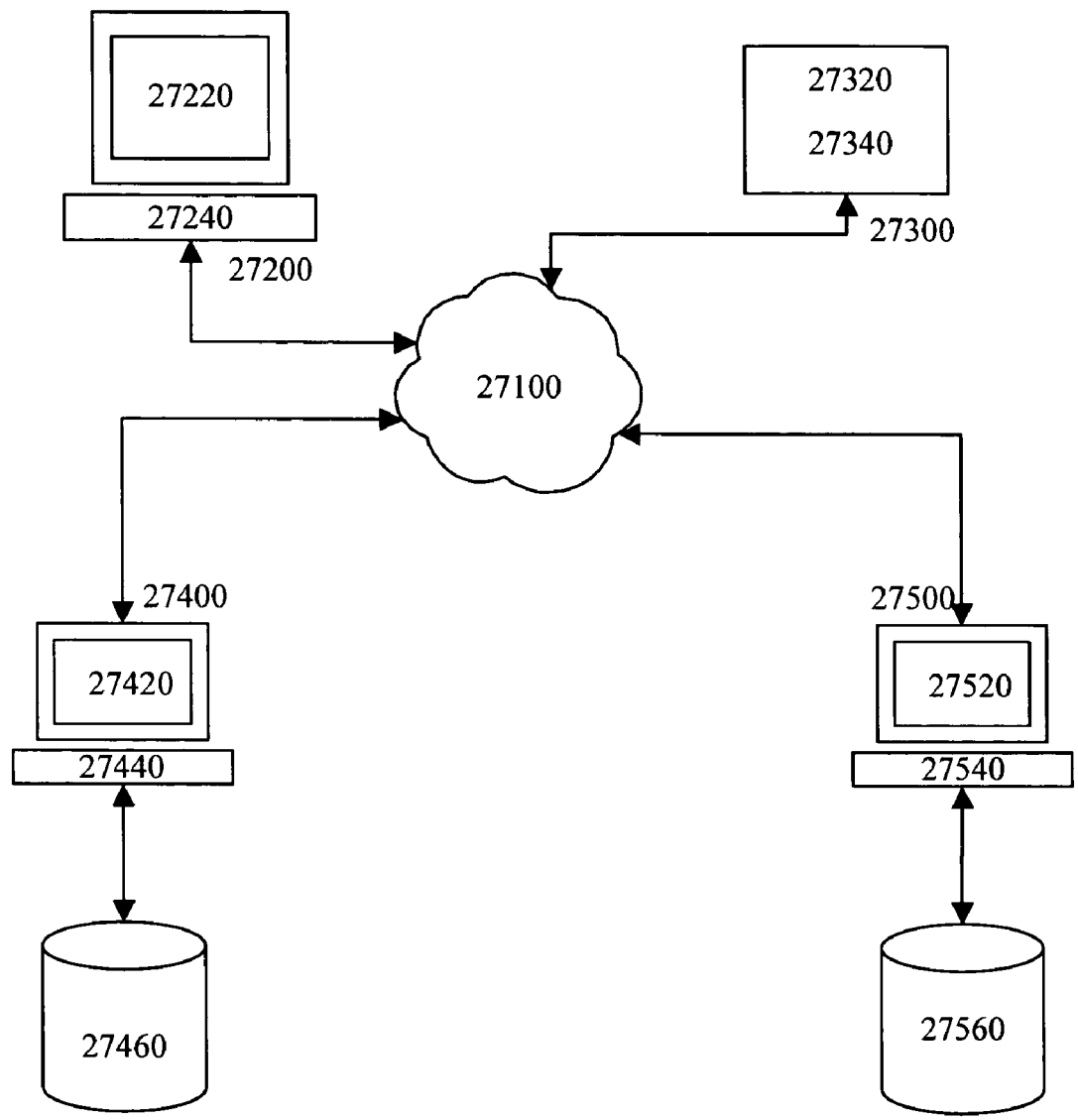
FIG. 27 is a block diagram of an exemplary embodiment of a system 27000.

FIG. 27 is a block diagram of an exemplary embodiment of a system 27000, which can comprise a magnetic resonance imaging system Magnetic Resonance Imaging Device (MRI) 27300. MRI 27300 can comprise a Magnetic Resonance Imaging Sensor 27320 and a Magnetic Resonance Imaging Detector 27340. MRI 27300 can be communicatively coupled to an information device 27200, which can comprise a user interface 27220 and a user program 27240. MRI 27300 can be communicatively coupled to a first server 27400, which can comprise a user interface 27420 and a user program 27440. First server 27400 can comprise and/or be communicatively coupled to a memory device 27460. MRI 27300 can be communicatively coupled to a second server 27500, which can comprise a user interface 27520 and a user program 27540. Second server 27500 can comprise and/or be communicatively coupled to a memory device 27560.

Via user interface 27220, user interface 27420, and/or user interface 27520 a user can view renderings and/or information regarding renderings of images derived from MRI 27300. User program 27420, user program 27440, and/or user program 27540 can be configured to receive and/or process information related to rendering images derived from MRI 27300.

Memory device 27460 and/or memory device 27560 can be machine readable media. Memory device 27460 and/or memory device 27560 can comprise machine instructions for activities comprising automatically causing a representation of body tissue to be rendered. For example, the body tissue can be a brain, portion of a brain, in-vivo bundle of brain fibers, lung, heart, liver, pancreas, kidney, arm, leg, stomach, digestive tract, spinal column, and/or lymphatic system, etc. The body tissue can be human, canine, feline, bovine, and/or related to any other type of animal, etc. The body tissue can be tracked via clusters. The clusters can each comprise a predetermined number of particles. Each particle of a particular cluster can be representative of a discreet path associated with the particular cluster in a tensor field. The discreet path can be a set of locations in the tensor field. The tensor field can be computed via a magnetic resonance imaging sensor. Each of the predetermined number of particles iteratively sampled from a probability function:

$$p_{tensor}(x_t \mid x_{t-1}) = \frac{1}{(2\pi)^{3/2}} \exp\left(-\frac{1}{2}(x_t - x_{t-1})^T D(x_{t-1})^{-1}(x_t - x_{t-1})\right)$$

where:
D(x) is a normalized tensor at location x, the normalized tensor obtained from the magnetic resonance imaging sensor;
t is a time interval associated with tracking the in-vivo bundle of brain fibers; and
x is a location associated with tracking the in-vivo bundle of brain fibers.

Each of the predetermined number of particles can have an associated weight computed from the following equation:

$$w_{0:t}^j = \frac{p(x_t^i \mid x_{t-1}^i)}{p_{tensor}(x_t^i \mid x_{t-1}^i)} w_{0:t-1}^j$$

where:
$w_{0:t}^i$ is a weight associated with particle i at time t;
t is a time interval associated with tracking the in-vivo bundle of brain fibers;
x is a location associated with tracking the in-vivo bundle of brain fibers;
$p_{tensor}$ is the probability function;

$$p(x_t \mid x_{t-1}) = p_{tensor}(x_t \mid x_{t-1}) \times p_{reg}(x_t \mid x_{t-1}) \times p_{fa}(x_t \mid x_{t-1})$$

$p_{reg}$ is a linearity probability derived from a distance between $x_{t-1}$-$x_{t-2}$ and $x_t$-$x_{t-1}$; and
$p_{fa}$ is a fractional anisotropy probability computed from fractional anisotropy at location $x_t$ determined from the normalized tensor.

Each of the clusters can be created from a first particle, and then via recursive additions of a next particle to a closest existing cluster if a determined distance between the next particle and the center of the closest existing cluster is smaller than a predetermined threshold.

Information device 27200, first server 27400, and/or second server 27500 can be configured to transmit a signal via network 27100. The signal can comprise machine instructions for automatically causing a representation of body tissue to be rendered. The body tissue can be tracked via clusters. The clusters can each comprise a predetermined number of particles. Each particle of a particular cluster can be representative of a discreet path associated with the particular cluster in a tensor field. The discreet path can be a set of locations in the tensor field. The tensor field can be computed via a magnetic resonance imaging sensor. Each of the predetermined number of particles iteratively sampled from a probability function:

$$p_{tensor}(x_t \mid x_{t-1}) = \frac{1}{(2\pi)^{3/2}} \exp\left(-\frac{1}{2}(x_t - x_{t-1})^T D(x_{t-1})^{-1}(x_t - x_{t-1})\right)$$

where:
D(x) is a normalized tensor at location x, the normalized tensor obtained from the magnetic resonance imaging sensor;
t is a time interval associated with tracking the in-vivo bundle of brain fibers; and
x is a location associated with tracking the in-vivo bundle of brain fibers.

Each of the predetermined number of particles can have an associated weight computed from the following equation $$w_{0:t}^j = \frac{p(x_t^i \mid x_{t-1}^i)}{p_{tensor}(x_t^i \mid x_{t-1}^i)} w_{0:t-1}^j$$

where:
$w_{0:t}^i$ is a weight associated with particle i at time t;
t is a time interval associated with tracking the in-vivo bundle of brain fibers;
x is a location associated with tracking the in-vivo bundle of brain fibers;
$p_{tensor}$ is the probability function;

$$p(x_t \mid x_{t-1}) = p_{tensor}(x_t \mid x_{t-1}) \times p_{reg}(x_t \mid x_{t-1}) \times p_{fa}(x_t \mid x_{t-1})$$

$p_{reg}$ is a linearity probability derived from a distance between $x_{t-1}$-$x_{t-2}$ and $x_t$-$x_{t-1}$; and
$p_{fa}$ is a fractional anisotropy probability computed from fractional anisotropy at location $x_t$ determined from the normalized tensor.

Each of the clusters can be created from a first particle, and then via recursive additions of a next particle to a closest existing cluster if a determined distance between the next particle and the center of the closest existing cluster is smaller than a predetermined threshold.

Figure 28:
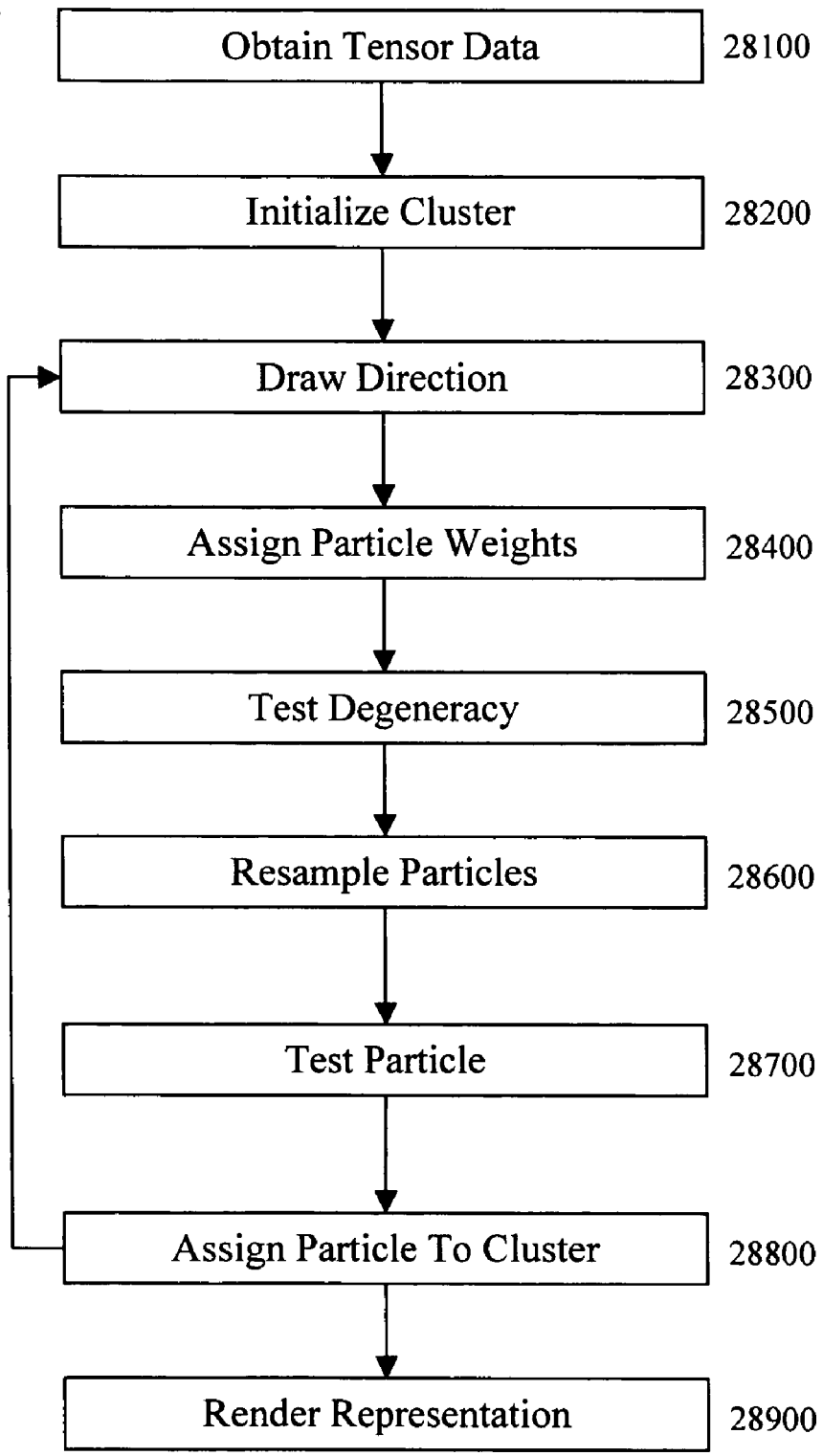
FIG. 28 is a flowchart of an exemplary embodiment of a method 28000.

FIG. 28 is a flowchart of an exemplary embodiment of a method 28000. At activity 28100, tensor data can be obtained. The tensor field can be obtained and/or computed from a magnetic resonance imaging sensor. The tensor data can be related to body tissue, such as an in-vivo bundle of brain fibers.

At activity 28200, clusters can be initialized. In certain exemplary embodiments, a predetermined distance between a point associated with a cluster, such as a center of the cluster, and a particle can be defined. The predetermined distance can be utilized to determine whether a particle should be added to a specific cluster. A cluster center can be determined and/or calculated. The cluster center can be determined based upon a mean of particles comprised in the cluster. A representation of the body tissue can be tracked via clusters. Each cluster can be initialized by initializing a set of particles at a seed point. Each cluster can be configured to track the body tissue beginning at the seed point.

The clusters can comprise a predetermined number of particles. Each particle of a particular cluster can be representative of a discreet path associated with the particular cluster in a tensor field. The discreet path can be a set of locations in the tensor field.

Each of the predetermined number of particles associated with a particular cluster can be sampled from a probability function:

$$p_{tensor}(x_t \mid x_{t-1}) = \frac{1}{(2\pi)^{3/2}} \exp\left(-\frac{1}{2}(x_t - x_{t-1})^T D(x_{t-1})^{-1}(x_t - x_{t-1})\right)$$

where:
D(x) is a normalized tensor at location x, the normalized tensor obtained from the magnetic resonance imaging sensor;
t is a time interval associated with tracking the in-vivo bundle of brain fibers; and
x is a location associated with tracking the in-vivo bundle of brain fibers The direction drawn from a selected particle can be related to a measured anisotropy associated with the selected particle and/or obtained from the tensor field. For each particle, a direction can be drawn based upon a probability distribution induced by the tensor field at a location of the particle. Each particle can be moved by a predefined step size in the drawn direction.

At activity 28300, a direction can be drawn from a particle. For each of the predetermined number of particles, a direction can be determined based upon a probability distribution induced by $p_{tensor}$ and moving each particle by a predetermined step size in the direction.

At activity 28400, particle weights can be assigned. Particle weights can be determined and/or assigned via an equation:

$$w_{0:t}^j = \frac{p(x_t^i | x_{t-1}^i)}{p_{tensor}(x_t^i | x_{t-1}^i)} w_{0:t-1}^j$$

where:

$w_{0:t}^i$ is a weight associated with particle i at time t;

t is a time interval associated with tracking the in-vivo bundle of brain fibers;

x is a location associated with tracking the in-vivo bundle of brain fibers;

$p_{tensor}$ is the probability function;

$p(x_t|x_{t-1}) = p_{tensor}(x_t|x_{t-1}) \times p_{reg}(x_t|x_{t-1}) \times p_{fa}(x_t|x_{t-1})$ $p_{reg}$ is a linearity probability derived from a distance between $x_{t-1}-x_{t-2}$ and $x_t-x_{t-1}$; and $p_{fa}$ is a fractional anisotropy probability computed from fractional anisotropy at location $x_t$ determined from the normalized tensor.

In certain exemplary embodiments, each weight can be normalized.

At activity 28500, degeneracy can be tested, which can, for example, help determine whether a particle should be removed from a cluster and/or be resampled. As another example, for each cluster, one or more particles can be removed whose weights are below a predefined threshold.

At activity 28600, particles can be resampled. For example, particles can be resampled responsive to a determined degeneracy of an evaluated particle.

At activity 28700, particles can be tested. In certain exemplary embodiments, a determined cluster can be removed if a count of particles comprised in the determined cluster is below a predetermined count threshold. If the determined cluster is removed, each particle from the determined cluster can be reassigned to a closest remaining cluster. In certain exemplary embodiments, a center of the closest existing cluster can be recalculated based upon a mean of particles comprised in the closest existing cluster.

At activity 28800, particles can be assigned to a cluster. Each of the clusters can be created from a first particle, and then via recursive additions of a next particle to a closest existing cluster if a determined distance between the next particle and the center of the closest existing cluster is smaller than a predetermined threshold. For each cluster, particles can be duplicated until each cluster contains the predetermined number of particles. The duplicated particles can be randomly selected according to their weights. Each cluster can have the predetermined number of particles maintained to allow branching without a loss of tracking power. In certain exemplary embodiments, a new cluster can be created if a distance between the next particle and the center of the closest existing cluster is above the predetermined threshold. After a particle is assigned to a cluster and/or a cluster is created, a new cluster center can be determined. The new cluster center can be based upon a mean of particles comprised in each cluster. If method 28000 is not terminated, activities can be repeated beginning at activity 28300. Method 28000 can be terminated when a probability is determined to be below a predetermined probability threshold. Method 28000 can be terminated when a boundary of the tensor field is reached.

At activity 28900, a representation can be rendered. The representation can be automatically rendered and/or can be automatically caused to be rendered. The representation can comprise a most likely fiber structure. The most likely fiber structure can comprise a path followed by particles associated with probabilities above a predetermined threshold.

Figure 29:
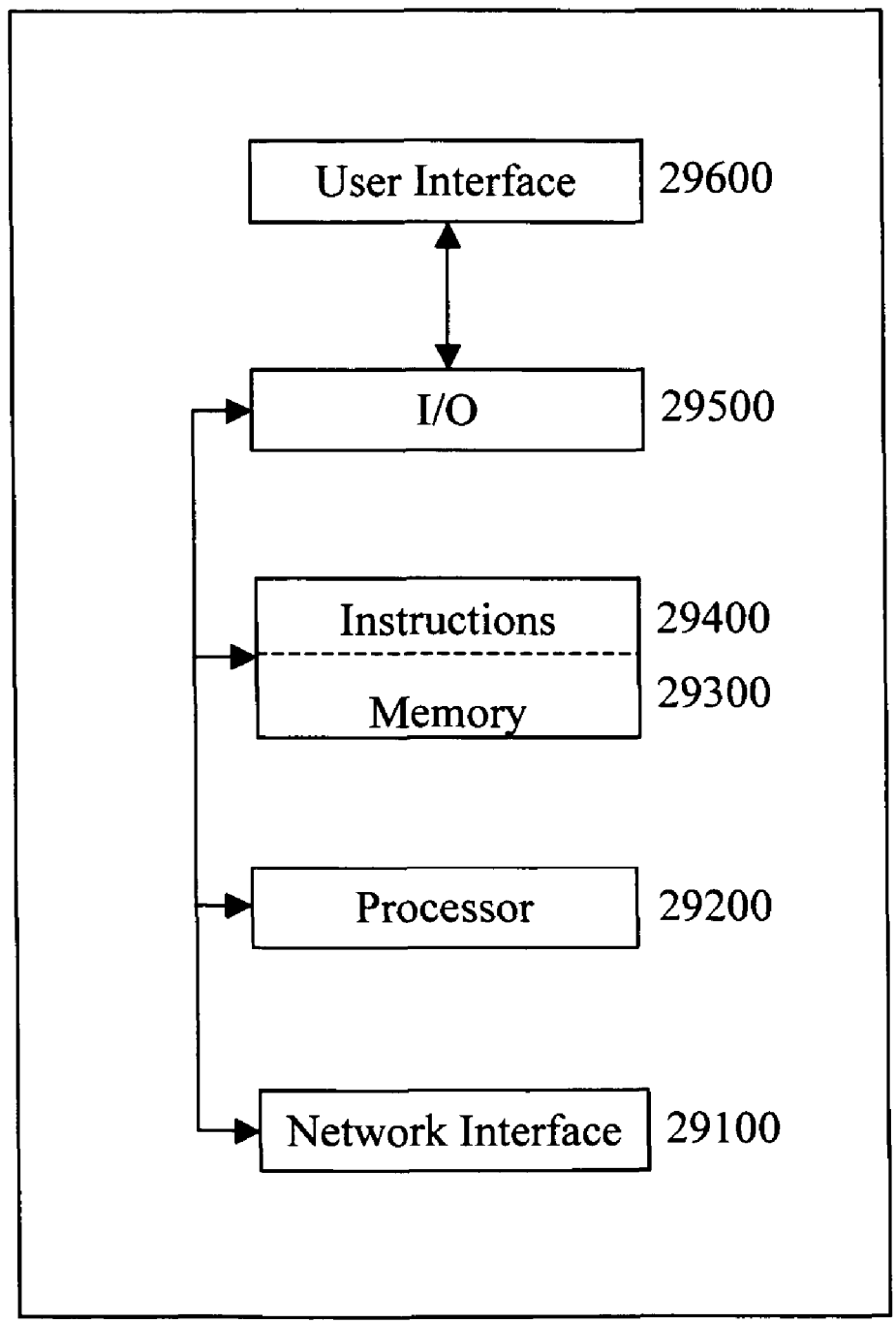
FIG. 29 is a block diagram of an exemplary embodiment of an information device 29000.

FIG. 29 is a block diagram of an exemplary embodiment of an information device 29000, which in certain operative embodiments can comprise, for example, information device 27200, first server 27400, and/or second server 27500 of FIG. 27. Information device 29000 can comprise any of numerous components, such as for example, one or more network interfaces 29100, one or more processors 29200, one or more memories 29300 containing instructions 29400, one or more input/output (I/O) devices 29500, and/or one or more user interfaces 29600 coupled to I/O device 29500, etc.

In certain exemplary embodiments, via one or more user interfaces 29600, such as a graphical user interface, a user can view a rendering of information related to an image determined from information obtained from an MRI system.

DEFINITIONS

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

activity—an action, act, step, and/or process or portion thereof.

adapted to—made suitable or fit for a specific use or situation.

add—to associate with a set.

adjacent—near to.

and/or—either in conjunction with or in alternative to.

anisotropy—a variation of aqueous diffusion depending on a direction in which it is measured.

apparatus—an appliance or device for a particular purpose.

approximate—nearly the same as.

approximation—an estimate that is nearly the same as.

assign—designate.

associate—to join, connect together, and/or relate.

associated with—related to.

automatically—acting or operating in a manner essentially independent of external influence or control. For example, an automatic light switch can turn on upon "seeing" a person in its view, without the person manually operating the light switch.

average—an approximation of a statistical expected value.

based upon—being derived from.

begin—to start.

boundary—a furthest extent of.

brain—a portion of a vertebrate central nervous system that is enclosed within a cranium, continuous with a spinal cord, and composed of gray matter and white matter.
branches—a secondary outgrowth or subdivision.
calculation—a determination of something by mathematical or logical methods.
can—is capable of, in at least some embodiments.
cause—to produce an effect.
center—a point that is substantially equally distant from the outer boundaries of something.
change—a transformation or transition from one state, condition, or phase to another.
closest—nearest.
cluster—a plurality of associated particles.
comprising—including but not limited to.
compute—to determine by mathematics.
configure—to make suitable or fit for a specific use or situation.
convert—to transform, adapt, and/or change.
correlation—a simultaneous and related change in value of two variables.
corresponding—accompanying and associated with something else.
count—a defined quantity.
create—to bring into being.
data—distinct pieces of information, usually formatted in a special or predetermined way and/or organized to express concepts.
data structure—an organization of a collection of data that allows the data to be manipulated effectively and/or a logical relationship among data elements that is designed to support specific data manipulation functions. A data structure can comprise metadata to describe the properties of the data structure. Examples of data structures can include: array, dictionary, graph, hash, heap, linked list, matrix, object, queue, ring, stack, tree, and/or vector.
decrease—to be smaller in magnitude.
define—to establish the outline, form, or structure of.
determine—ascertain, obtain, and/or calculate.
device—a machine, manufacture, and/or collection thereof.
direction—a distance-independent relationship between two points in space that specifies the angular position of either with respect to the other.
distance—a spatial separation between to points.
distinct—distinguishable from all others.
duplicate—to copy.
eigenvector—in linear algebra, eigenvectors (from the German eigen meaning "inherent, characteristic") of a linear operator are non-zero vectors which, when operated on by the operator, result in a scalar multiple of themselves. The scalar is then called the eigenvalue associated with the eigenvector.
equation—a statement asserting the equality of two expressions, usually written as a linear array of symbols that are separated into left and right sides and joined by an equal sign.
estimate—to calculate and/or determine approximately and/or tentatively.
fiber—a slender and greatly elongated component of the human brain, a neuron, and/or an axon.
fractional—constituting or comprising a part or fraction of a possible whole or entirety.
function—a defined mathematical relationship.
generate—to create, produce, give rise to, and/or bring into existence.
haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.
image—an at least two-dimensional representation of an object and/or phenomenon.
induce—to bring about or cause to occur.
information device—any device capable of processing information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.
initial—at a beginning.
initialize—to prepare something for use and/or some future event.
input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.
inside—within a determined boundary.
integrate—to calculate as a summation.
intrinsic—belonging to a thing by a very nature of the thing.
in-vivo—within a living organism.
iteratively—repeatedly.
larger—greater in magnitude.
less than—smaller in magnitude.
local—associated with a predetermined area or region.
location—a place substantially approximating where something physically exists.
machine instructions—directions adapted to cause a machine, such as an information device, to perform a particular operation or function. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine readable medium—a physical structure from which a machine can obtain data and/or information. Examples include a memory, punch cards, etc.

magnetic resonance imaging—a procedure in which radio waves and a magnet linked to a computer are used to detect characteristics of a living organism.

magnitude—greatness in size or extent.

may—is allowed and/or permitted to, in at least some embodiments.

mean—a mathematical average.

measurement—a dimension, quantification, and/or capacity, etc. determined by observation.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

most likely—having a highest probability of occurrence.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, Ethernet card, cable modem, digital subscriber line interface, bridge, hub, router, or other similar device.

new—not previously defined.

noise image—representations of an image comprising one or more random voxels.

normalize—to cause to numerically conform to a standard.

obtain—to receive or determine.

packet—a discrete instance of communication.

particle—a sample from a probability space usable in a model as a step in a path in a tensor field and associated with a measured value from a magnetic resonance imaging sensor.

path—a route along which something moves.

plurality—the state of being plural and/or more than one.

point—a defined location in at least a two-dimensional system.

positive—greater than approximately zero.

predefined—established in advance.

predetermined—established in advance.

probability—a quantitative representation of a likelihood of an occurrence.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

project—to calculate, estimate, or predict.

projection direction—a direction in which a voxel, particle, and/or point is determined to be associated with another related voxel, particle, and/or point.

provide—to furnish, supply, give, and/or make available.

random—Of or relating to an event in which a plurality of outcomes are approximately equally likely.

reassign—to change a designation from a first designation to a second designation.

reach—to arrive at.

receive—to get as a signal, take, acquire, and/or obtain.

recommend—to suggest, praise, commend, and/or endorse.

recursively—repetitively.

remove—to delete from an associated set.

render—make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

represent—to be considered as an acceptable equivalent of.

representation—an approximation of an equivalent of.

request—to express a desire for and/or ask for.

Runge-Kutta integration—an iterative method for approximating solutions to ordinary differential equations.

seed—a source or beginning.

select—to make a choice or selection from alternatives.

sensor—a device used to measure a physical quantity (e.g., temperature, pressure, capacitance, and/or loudness, etc.) and convert that physical quantity into a signal of some kind (e.g., voltage, current, power, etc.). A sensor can be any instrument such as, for example, any instrument measuring pressure, temperature, flow, mass, heat, light, sound, humidity, proximity, position, velocity, vibration, voltage, current, capacitance, resistance, inductance, and/or electromagnetic radiation, etc. Such instruments can comprise, for example, proximity switches, photo sensors, thermocouples, level indicating devices, speed sensors, electrical voltage indicators, electrical current indicators, on/off indicators, and/or flowmeters, etc.

set—a related plurality.

signal—information encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal can be synchronous, asynchronous, hard real-time, soft real-time, non-real time, continuously generated, continuously varying, analog, discretely generated, discretely varying, quantized, digital, continuously measured, and/or discretely measured, etc.

size—a magnitude of an object or entity.

slice—a two dimensional section of a three dimensional object.

smaller—lower in magnitude.

step—one of a series of actions, processes, or measures taken to achieve a goal.

store—to place, hold, and/or retain data, typically in a memory.

streamline image—a representation of an object based upon a projection of one or more voxels, particles, and/or points in a determined direction.

streamline steps—iterations over which a voxel, particle, and/or point is projected from a point of origin.

structure—a manner in which parts form a whole.

substantially—to a great extent or degree.

successive—following in order.

system—a collection of mechanisms, devices, data, and/or instructions, the collection designed to perform one or more specific functions.

tensor—a certain kind of geometrical entity, or alternatively a generalized "quantity". The tensor concept includes the ideas of scalar, vector, and linear operator. Tensors can be described in terms of coordinate systems, as arrays of scalars, but are defined so as to be independent of any chosen frame of reference.

tensor field—a plurality of related tensors.

terminate—to end.

three dimensional—definable via coordinates relative to three mutually perpendicular axes.

three dimensional coordinates—values indicative of a position of a point in a defined space associated with three mutually perpendicular coordinate axes.

time interval—a finite period of time between a starting time and an ending time.

tissue—an aggregation of morphologically similar cells and associated intercellular matter acting together to perform one or more specific functions in the body.

track—to follow a path of.

transmit—to send as a signal, provide, furnish, and/or supply.

two dimensional—definable via coordinates relative to two perpendicular axes.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

value—an assigned or calculated numerical quantity.

vector field—a plurality of related vectors.

via—by way of and/or utilizing.

voxel—a finite volume in three dimensional space representing a resolvable and/or renderable volume associated with a predetermined system.

weight—a value indicative of importance.

Note

Still other practical and useful embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application.

Thus, regardless of the content of any portion (e.g., title, field, background, summary, abstract, drawing figure, etc.) of this application, unless clearly specified to the contrary, such as via an explicit definition, assertion, or argument, with respect to any claim, whether of this application and/or any claim of any application claiming priority hereto, and whether originally presented or otherwise:

- there is no requirement for the inclusion of any particular described or illustrated characteristic, function, activity, or element, any particular sequence of activities, or any particular interrelationship of elements;
- any elements can be integrated, segregated, and/or duplicated;
- any activity can be repeated, performed by multiple entities, and/or performed in multiple jurisdictions; and
- any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

Any information in any material (e.g., a U.S. patent, U.S. patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

Accordingly, the descriptions and drawings are to be regarded as illustrative in nature, and not as restrictive.

What is claimed is:

1. A method comprising:
   automatically causing a representation of an in-vivo bundle of brain fibers to be rendered, said in-vivo bundle of brain fibers tracked via clusters, said clusters each comprising a predetermined number of particles, each particle of a particular cluster representative of a discreet path associated with said particular cluster in a tensor field, said discreet path a set of locations in said tensor field, said tensor field computed via a magnetic resonance imaging sensor, said representation comprising a most likely fiber structure, said most likely fiber structure comprising a path followed by a subset of said particles, said subset associated with particle probabilities above a predetermined threshold, each of said predetermined number of particles iteratively sampled via a probability function:

$$p_{tensor}(x_t \mid x_{t-1}) = \frac{1}{(2\pi)^{3/2}} \exp\left(-\frac{1}{2}(x_t - x_{t-1})^T D(x_{t-1})^{-1}(x_t - x_{t-1})\right)$$

where:
   D(x) is a normalized tensor at location x, said normalized tensor obtained from said magnetic resonance imaging sensor;
   t is a time interval associated with tracking said in-vivo bundle of brain fibers; and
   x is a location associated with tracking said in-vivo bundle of brain fibers;
each of said predetermined number of particles having an associated weight computed from an equation:

$$w_{0:t}^j = \frac{p(x_t^i \mid x_{t-1}^i)}{p_{tensor}(x_t^i \mid x_{t-1}^i)} w_{0:t-1}^j$$

where:
   $w_{0:t}^i$ is a weight associated with particle i at time t;
   t is a time interval associated with tracking said in-vivo bundle of brain fibers;
   $x^i$ is a location associated with tracking said in-vivo bundle of brain fibers associated with particle i;
   $p_{tensor}$ is obtained from said probability function;

$$p(x_t \mid x_{t-1}) = p_{tensor}(x_t \mid x_{t-1}) \times p_{reg}(x_t \mid x_{t-1}) \times p_{fa}(x_t \mid x_{t-1})$$

where:
   $p_{reg}$ is a probability derived from a distance between $x_{t-1} - x_{t-2}$ and $x_t - x_{t-1}$; and
   $p_{fa}$ is a fractional anisotropy probability computed from fractional anisotropy at location $x_t$ determined from said normalized tensor;
each of said clusters created from a first particle and via recursive additions of a next particle to a closest existing cluster if a determined distance between said next particle and a center of said closest existing cluster is smaller than said predetermined threshold;
and
iteratively sampling each of said predetermined number of particles via said probability function.

2. The method of claim 1, further comprising:
obtaining said tensor field from said magnetic resonance imaging sensor.

3. The method of claim 1, further comprising:
initializing a set of particles at a seed point, a count of said set of particles being predetermined; and
tracking said in-vivo bundle of brain fibers beginning at said seed point.

4. The method of claim 1, further comprising:
for each of said predetermined number of particles, determining a projection direction based upon a probability distribution induced by $p_{tensor}$ and moving each particle by a predetermined step size in said projection direction.

5. The method of claim 1, further comprising:
calculating each weight via said weight equation.

6. The method of claim 1, further comprising:
calculating each weight via said weight equation; and
normalizing each weight.

7. The method of claim 1, further comprising:
for each cluster, removing particles whose weights are below a predefined threshold.

8. The method of claim 1, further comprising:
for each cluster, duplicating particles until each cluster contains said predetermined number of particles, said duplicated particles randomly selected according to their weights; and
maintaining said predetermined number of particles in each cluster to branch without a loss of tracking power.

9. The method of claim 1, further comprising:
defining said predetermined distance.

10. The method of claim 1, further comprising:
creating a new cluster if a distance between said next particle and said center of closest existing cluster is above said predetermined threshold.

11. The method of claim 1, further comprising:
determining a center of each cluster.

12. The method of claim 1, further comprising:
determining a center of each cluster based upon a mean number of particles comprised in each cluster.

13. The method of claim 1, further comprising:
removing a predetermined cluster if a count of particles comprised in said predetermined cluster is below a predetermined count threshold; and
reassigning each particle from said predetermined cluster to a closest remaining cluster.

14. The method of claim 1, further comprising:
recalculating said center of said closest existing cluster based upon a mean number of particles comprised in said closest existing cluster.

15. The method of claim 1, further comprising:
terminating said method when a particle probability is determined to be below a predetermined probability threshold.

16. A machine-readable medium comprising machine instructions for activities comprising:
automatically causing a representation of an in-vivo bundle of brain fibers to be rendered, said in-vivo bundle of brain fibers tracked via clusters, said clusters each comprising a predetermined number of particles, each particle of a particular cluster representative of a discreet path associated with said particular cluster in a tensor field, said discreet path a set of locations in said tensor field, said tensor field computed via a magnetic resonance imaging sensor, said representation comprising a most likely fiber structure, said most likely fiber structure comprising a path followed by a subset of said particles, said subset associated with particle probabilities above a predetermined threshold, each of said predetermined number of particles iteratively sampled via a probability function:

$$p_{tensor}(x_t \mid x_{t-1}) = \frac{1}{(2\pi)^{3/2}} \exp\left(-\frac{1}{2}(x_t - x_{t-1})^T D(x_{t-1})^{-1}(x_t - x_{t-1})\right)$$

where:
D(x) is a normalized tensor at location x, said normalized tensor obtained from said magnetic resonance imaging sensor;
t is a time interval associated with tracking said in-vivo bundle of brain fibers; and
x is a location associated with tracking said in-vivo bundle of brain fibers;
each of said predetermined number of particles having an associated weight computed from an equation:

$$w_{0:t}^j = \frac{p(x_t^j \mid x_{t-1}^j)}{p_{tensor}(x_t^j \mid x_{t-1}^j)} w_{0:t-1}^j$$

where:
$w_{0:t}^i$ is a weight associated with particle i at time t;
t is a time interval associated with tracking said in-vivo bundle of brain fibers;
$x^i$ is a location associated with tracking said in-vivo bundle of brain fibers associated with particle i;
$P_{tensor}$ is obtained from said probability function;

$$p(x_t \mid x_{t-1}) = p_{tensor}(x_t \mid x_{t-1}) \times p_{reg}(x_t \mid x_{t-1}) \times p_{fa}(x_t \mid x_{t-1})$$

where:
$P_{reg}$ is a probability derived from a distance between $x_{t-1} - x_{t-2}$ and $x_t - x_{t-1}$; and
$p_{fa}$ is a fractional anisotropy probability computed from fractional anisotropy at location $x_t$ determined from said normalized tensor;
each of said clusters created from a first particle and via recursive additions of a next particle to a closest existing cluster if a determined distance between said next particle and a center of said closest existing cluster is smaller than a predetermined threshold
and
iteratively sampling each of said predetermined number of particles via said probability function.

17. A method comprising:
via a magnetic resonance imaging sensor, transforming sensed molecular placement data into a tensor field that is associated with a physical structure of a body tissue, said transforming comprising:
calculating a discreet path associated with a particular cluster in said tensor field, said particular cluster one of a plurality of clusters, said clusters each comprising a predetermined number of particles, said discreet path a set of locations in said tensor field, said tensor field comprising a most likely fiber structure, said most likely fiber structure comprising a path followed by a subset of said particles, said subset associated with particle probabilities above a predetermined threshold, each of said predetermined number of particles iteratively sampled via a probability function:

$$p_{tensor}(x_t \mid x_{t-1}) = \frac{1}{(2\pi)^{\frac{3}{2}}} \exp\left[-\frac{1}{2}(x_t - x_{t-1})^T D(x_{t-1})^{-1}(x_t - x_{t-1})\right]$$

where: D(x) is a normalized tensor at location x, said normalized tensor obtained from said magnetic resonance imaging sensor; t is a time interval associated with tracking said in-vivo bundle of brain fibers; and x is a location associated with tracking said in-vivo bundle of brain fibers;
each of said predetermined number of particles having an associated weight, said weight calculated using:
a previous weight calculated at an earlier time,
said time interval,
a probability derived from a distance, and
a fractional anisotropy probability computed from a fractional anisotropy at said location;
each of said clusters created from a first particle and via recursive additions of a next particle to a closest existing cluster if a determined distance between said next particle and a center of said closest existing cluster is smaller than a predetermined threshold.

* * * * *